(12) United States Patent
Okusa et al.

(10) Patent No.: US 7,396,825 B2
(45) Date of Patent: Jul. 8, 2008

(54) AGONISTS OF A2A ADENOSINE RECEPTORS FOR TREATMENT OF DIABETIC NEPHROPATHY

(75) Inventors: Mark D. Okusa, Charlottesville, VA (US); Joel M. Linden, Charlottesville, VA (US); Timothy L. Macdonald, Charlottesville, VA (US); Alaa S. Awad, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 385 days.

(21) Appl. No.: 11/121,169

(22) Filed: May 3, 2005

(65) Prior Publication Data

US 2005/0261236 A1 Nov. 24, 2005

Related U.S. Application Data

(60) Provisional application No. 60/567,465, filed on May 3, 2004.

(51) Int. Cl.
*A01N 43/04* (2006.01)
*A61K 31/70* (2006.01)
*C07H 19/00* (2006.01)
*C07H 19/22* (2006.01)

(52) U.S. Cl. ............................ 514/45; 514/43; 514/48

(58) Field of Classification Search ....................... None
See application file for complete search history.

(56) References Cited

U.S. PATENT DOCUMENTS 6,531,457 B2  3/2003  Linden et al.

FOREIGN PATENT DOCUMENTS

WO   WO-2005/107463 A1   11/2005

OTHER PUBLICATIONS

Okusa et al. Kidney International (2001), vol. 59, pp. 2114-2125.*
Pflueger et al. Am. J. Physiol Renal Physiol. (1999), vol. 276, pp. 340-346.*
"International Search Report for Application No. PCT/US05/15241", (Aug. 19, 2005),3 pgs.
Okusa, M D., "Enhanced Protection from Renal Ischemia: Reperfusion Injury With A2A-Adenosine Receptor Activation and PDE 4 Inhibition", *Kidney International*, 59(6), (2001),2114-2125.
Okusa, Mark D., "Selective A2A adenosine receptor activation reduces ischemia-reperfusion injury in rat kidney", *Am. J. Physiol.*, vol. 277 (3, Pt 2), (1999),F404-F412.

* cited by examiner

*Primary Examiner*—Patrick Lewis
(74) *Attorney, Agent, or Firm*—Schwegman, Lundberg, & Woessner, P.A.

(57) ABSTRACT

The present invention provides a therapeutic method for treating diabetic kidney disease, e.g., diabetic nephropathy that includes the administration of an effective amount of an $A_{2A}$ adenosine receptor agonist. Optionally, the method includes administration of a type IV PDE inhibitor.

58 Claims, 6 Drawing Sheets

AGONISTS OF A2A ADENOSINE RECEPTORS FOR TREATMENT OF DIABETIC NEPHROPATHY

CROSS REFERENCE TO RELATED APPLICATIONS

This application claims priority of U.S. provisional patent application Ser. No. 60/567,465, filed May 3, 2004, which application is incorporated by reference herein.

GOVERNMENT FUNDING

The invention described herein was made with government support under Grant Number DK58413-02A1 awarded by the National Institute of Health. The United States Government has certain rights in the invention.

FIELD OF THE INVENTION

The present invention provides a method for treating inflammation caused by diabetes particularly, diabetic kidney disease, e.g., diabetic nephropathy.

BACKGROUND OF THE INVENTION

Diabetes is the most common cause of end stage renal disease (ESRD) in the United States, accounting for ~40% of the cases of renal failure at the time of initiation of dialysis or transplantation. Diabetic nephropathy (DN) is a kidney disease that can occur as a result of diabetes and is a leading cause of kidney failure and ESRD. Increased demand upon the kidneys is indicated by an above-normal glomerular filtration rate (GFR). High glucose levels are believed to cause damage to the glomeruous where blood enters the kidney. For patients suffering from DN, the delicate filtering system in the kidney becomes damaged, initially becoming leaky to large blood proteins such as albumin which are then lost in urine.

Typically, DN is prevented or controlled by controlling the blood glucose level. This has been used to prevent the development and slow the progression of diabetic nephropathy, as well as the other complications of diabetes. DN begins with a tiny amount of protein appearing in the urine—this is called microalbuminuria. Over about 10-15 years proteinuria can increase, and nephrotic syndrome may develop. The development of proteinuria reduces the kidneys' ability to remove poisons from the blood such that 5-10 years later the kidneys are almost completely unable to remove these poisons from the blood. This is called "end-stage renal disease" (ESRD), and, unless treated, can be fatal.

An abnormal condition that can develop or worsen in DN patients is high blood pressure. This can be the first symptom (abnormality) to develop. Diabetic nephropathy is also an indication of worsening blood vessel disease throughout the body. Diabetic eye disease is usually present by this stage indicating damage to smaller blood vessels. Larger blood vessels (arteries) are almost always affected. This can lead to heart attacks, strokes, and circulatory disease occurring more often and at a younger age than usual. Commonly diabetes will have also resulted in damage to small nerves causing "diabetic peripheral nephropathy" and "autonomic neuropathy". Thus, Diabetic nephropathy (DN) is associated with markedly higher morbidity and mortality rates.

Current methods for treating DN include managing blood pressure. This usually requires more than one type of blood pressure medicine to achieve. Two classes of drug used to control blood pressure deserve special mention. These are the Angiotensin-Converting Enzyme (ACE) inhibitors and angiotensin II (AT II) receptor antagonists. Many studies have documented the greater potency of ACE inhibitors at reducing proteinuria and the progression of kidney disease compared to other classes of drug. These drugs not only reduce blood pressure in the large blood vessels, but also directly in the kidneys' filtering system (called glomeruli). Although these drugs tend to be preferentially used, they need to be monitored as they may have a detrimental effect on some people. It is thought that AT II receptor antagonists will have a similar effect, and these are often used in those unable to tolerate ACE inhibitors.

Accordingly, there is a need for the development of additional methods and suitable pharmaceutical agents useful in therapy for treatment and/or prevention of diabetic kidney disease particularly diabetic nephropathy. There is currently a need for a method to treat renal injury associated with diabetic kidney disease, such as, for example, diabetic nephropathy and renal injury associated with diabetic nephropathy.

SUMMARY OF THE INVENTION

The present invention provides a therapeutic method for treating diabetic kidney disease, e.g., diabetic nephropathy comprising the administration to a patient in need thereof, an effective amount an $A_{2A}$ adenosine receptor agonist. The beneficial effects of $A_{2A}$AR agonists have been documented in vivo, in experimental models using rats.

Agonists of $A_{2A}$ adenosine receptors are useful for treatment and/or prevent renal diabetic nephropathy. The effects of adenosine $A_{2A}$ agonists can be enhanced by type IV phosphodiesterase inhibitors such as, for example, rolipram.

The invention also provides for the use of an $A_{2A}$ adenosine receptor agonist compound in medical therapy (e.g., for use in the treatment of diabetic kidney disease, such as, diabetic nephropathy, as well as the use of an $A_{2A}$ adenosine receptor agonist compound for the manufacture of a medicament for reducing inflammation caused by diabetes treatment thereof in a mammal, such as a human.

DETAILED DESCRIPTION OF THE INVENTION

Figure 1:
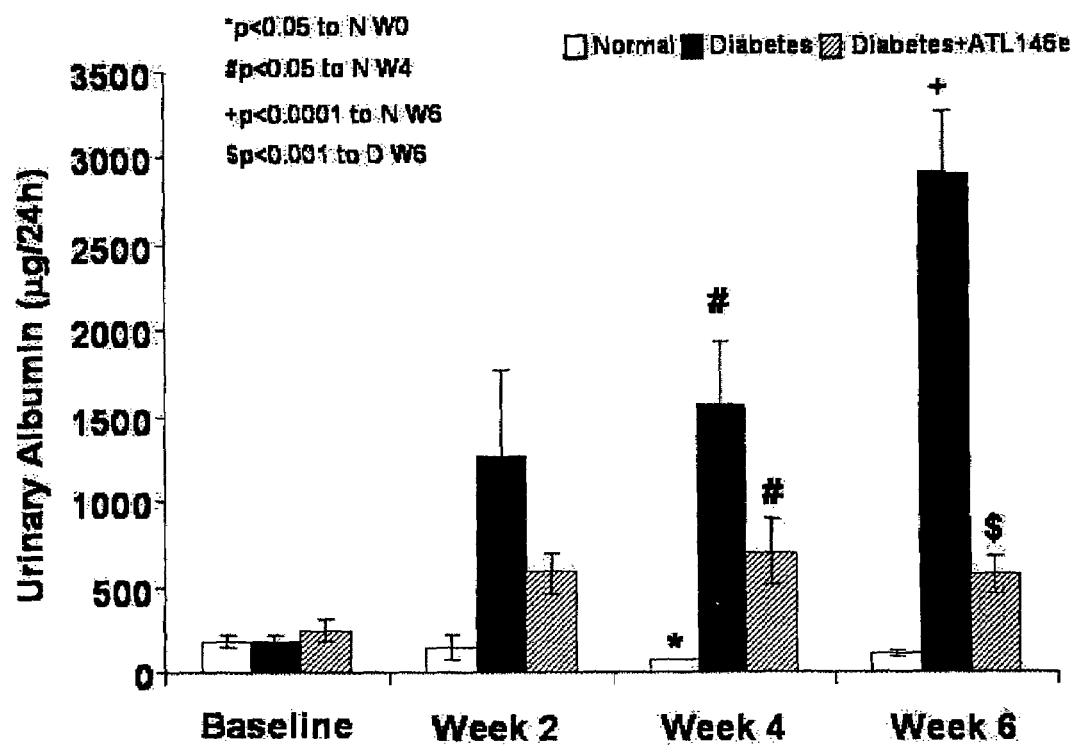
FIGS. 1-5 illustrate the use of an $A_{2A}$ AR agonist (ATL146e) in the treatment of prevention of diabetic nephropathy.

The present invention provides a therapeutic method for treating diabetic kidney disease, e.g., diabetic nephropathy comprising the administration to a patient in need thereof, an effective amount an $A_{2A}$ adenosine receptor agonist. Agonists of $A_{2A}$ adenosine receptors can be used for treatment and/or prevent renal diabetic nephropathy. The effects of adenosine $A_{2A}$ agonists can be enhanced by type IV phosphodiesterase inhibitors such as, for example, rolipram.

In another embodiment, the invention provides for the use of an $A_{2A}$ adenosine receptor agonist compound in medical therapy (e.g., for use in the treatment of diabetic kidney disease, such as, diabetic nephropathy, as well as the use of an $A_{2A}$ adenosine receptor agonist compound for the manufacture of a medicament for reducing inflammation caused by diabetes treatment thereof in a mammal, such as a human.

The invention provides a general method for treating DN by administering an effective amount of an $A_{2A}$ adenosine receptor agonist to a patient in need thereof such treatment. There are a large number of adenosine $A_{2A}$ receptor agonists known in the art. Several groups of $A_{2A}$ adenosine receptor agonists are disclosed herein. However, a person skilled in the art can make additional $A_{2A}$ receptor agonists without great difficulty. The effectiveness of $A_{2A}$ adenosine receptor agonists against diabetic nephropathy would not have been predicted on the basis of the uses known for $A_{2A}$ receptor agonists. There is scientific reason for believing that the effectiveness of $A_{2A}$ adenosine receptor agonists is a general property of these compounds and not merely a property specific to the actual compound tested herein.

Selective adenosine $A_{2A}$ receptor agonists can be identified by the ability of the selective adenosine $A_{2A}$ receptor antagonist ZM 241385 to block their activity of the $A_{2A}$ receptor agonist in known in vitro or in vivo models where the known $A_{2A}$ receptors are shown to be effective.

The following definitions are used, unless otherwise described. Halo is fluoro, chloro, bromo, or iodo. Alkyl, alkoxy, aralkyl, alkylaryl, etc. denote both straight and branched alkyl groups; but reference to an individual radical such as "propyl" embraces only the straight chain radical, a branched chain isomer such as "isopropyl" being specifically referred to. Aryl includes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, ($C_1$-$C_4$)alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

It will be appreciated by those skilled in the art that the compounds of formulas (I), (II), (III), and (IV) have more than one chiral center and may be isolated in optically active and racemic forms. Preferably, the riboside moiety of the compounds is derived from D-ribose, i.e., the 3',4'-hydroxyl groups are alpha to the sugar ring and the 2' and 5' groups is beta (3R, 4S, 2R, 5S). When the two groups on the cyclohexyl group are in the 1- and 4-position, they are preferably trans. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, or enzymatic techniques, by synthesis from optically-active starting materials, by chiral synthesis, or by chromatographic separation using a chiral stationary phase) and how to determine adenosine agonist activity using the tests described herein, or using other similar tests which are well known in the art.

Specific and preferred values listed below for radicals, substituents, and ranges, are for illustration only; they do not exclude other defined values or other values within defined ranges for the radicals and substituents.

Specifically, ($C_1$-$C_8$)alkyl can be methyl, ethyl, propyl, isopropyl, butyl, iso-butyl, sec-butyl, pentyl, 3-pentyl, hexyl, heptyl or octyl. As used herein, the term "cycloalkyl" encompasses bicycloalkyl (norbornyl, 2.2.2-bicyclooctyl, etc.) and tricycloalkyl (adamantyl, etc.), optionally comprising 1-2 N, O or S. Cycloalkyl also encompasses (cycloalkyl)alkyl. Thus, ($C_3$-$C_8$)cycloalkyl can be cyclopropyl, cyclobutyl, cyclopentyl, cyclohexyl,cycloheptyl, cyclooctyl, and the like. $C_3$-$C_7$ Cycloalkenyl can be cyclopropenyl, cyclobutenyl, cyclopentenyl, cyclohexenyl,cycloheptenyl, and the like. ($C_1$-$C_8$) Alkoxy can be methoxy, ethoxy, propoxy, isopropoxy, butoxy, iso-butoxy, sec-butoxy, pentoxy, 3-pentoxy, or hexyloxy; ($C_2$-$C_4$)alkenyl can be vinyl, allyl, 1-propenyl, 2-propenyl, 1-butenyl, 2-butenyl, 3-butenyl; ($C_1$-$C_6$)alkanoyl can be acetyl, propanoyl or butanoyl; halo($C_1$-$C_6$)alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy($C_1$-$C_6$)alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; ($C_1$-$C_6$)alkoxycarbonyl ($—CO_2R^2$) can be methoxycarbonyl, ethoxycarbonyl, propoxycarbonyl, isopropoxycarbonyl, butoxycarbonyl, pentoxycarbonyl, or hexyloxycarbonyl; ($C_1$-$C_6$)alkylthio can be methylthio, ethylthio, propylthio, isopropylthio, butylthio, isobutylthio, pentylthio, or hexylthio; aryl can be phenyl, indenyl, or naphthyl; and heteroaryl can be furyl, imidazolyl, triazolyl, triazinyl, oxazoyl, isoxazoyl, thiazolyl, isothiazolyl, pyraxolyl, pyrrolyl, pyrazinyl, tetrazolyl, puridyl (or its N-oxide), thientyl, pyrimidinyl (or its N-oxide), indolyl, isoquinolyl (or its N-oxide) or quinolyl (or its N-oxide).

Aryl denotes a phenyl radical or an ortho-fused bicyclic carbocyclic radical having about nine to ten ring atoms in which at least one ring is aromatic. Heteroaryl denotes a radical of a monocyclic aromatic ring containing five or six ring atoms consisting of carbon and 1, 2, 3, or 4 heteroatoms each selected from the group consisting of non-peroxide oxygen, sulfur, and N(Y) wherein Y is absent or is H, O, ($C_1$-$C_8$) alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

The term "heterocycle" generally represents a non aromatic heterocyclic group, having from 3 to about 10 ring atoms, which can be saturated or partially unsaturated, containing at least one heteroatom (e.g., 1, 2, or 3) selected from the group consisting of oxygen, nitrogen, and sulfur. Specific, "heterocycle" groups include monocyclic, bicyclic, or tricyclic groups containing one or more heteroatoms selected from the group consisting of oxygen, nitrogen, and sulfur. A "heterocycle" group also can include one or more oxo groups ($═O$) attached to a ring atom. Non-limiting examples of heterocycle groups include 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuelidine, thiomorpholine, and the like.

The term "alkylene" refers to a divalent straight or branched hydrocarbon chain (e.g ethylene —$CH_2CH_2$—).

The term "aryl($C_1$-$C_8$)alkylene" for example includes benzyl, phenethyl, 3-phenylpropyl, naphthylmethyl and the like.

As used herein, the term "treatment" or "treating," to the extent it relates to a disease or condition includes preventing the disease or condition from occurring, inhibiting the disease or condition, eliminating the disease or condition, and/or relieving one or more symptoms of the disease or condition.

As used herein the term "in conjunction with" refers to co-administration of a pharmaceutical agent, such as, for example, a PDE IV inhibitor or other pharmaceutical agent with the $A_{2A}$ adenosine receptor agonist. The agents and the $A_{2A}$ adenosine receptor agonists can be administered either simultaneously or as a mixture or they can be administered subsequently. The subsequent administration of the $A_{2A}$ adenosine receptor agonists can be prior to the agent, within minutes or up to about 48 hours after the administration of the agent. Preferably the administration of the $A_{2A}$ adenosine receptor agonists will be within about 24 hours and more preferably within about 12 hours.

The carbon atom content of various hydrocarbon-containing moieties is indicated by a prefix designating the minimum and maximum number of carbon atoms in the moiety, i.e., the prefix $C_i$-$C_j$ indicates a moiety of the integer "i" to the integer "j" carbon atoms, inclusive. Thus, for example, $(C_1$-$C_8)$alkyl refers to alkyl of one to eight carbon atoms, inclusive.

The compounds of the present invention are generally named according to the IUPAC or CAS nomenclature system. Abbreviations which are well known to one of ordinary skill in the art may be used (e.g., "Ph" for phenyl, "Me" for methyl, "Et" for ethyl, "h" for hour or hours and "rt" for room temperature).

In one embodiment, agonists of $A_{2A}$ adenosine receptors useful to practice the present invention include compounds having the formula (I):

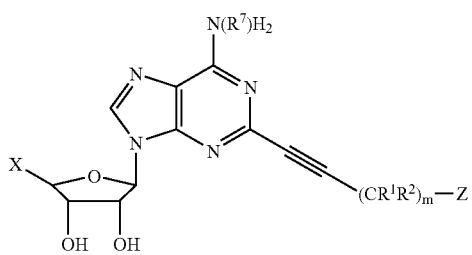

(I)

wherein

Z is $CR^3R^4R^5$ or $NR^4R^5$; each $R^1$ is independently hydrogen, halo, —$OR^a$, —$SR^a$, $(C_1$-$C_8)$alkyl, cyano, nitro, trifluoromethyl, trifluoromethoxy, $(C_3$-$C_8)$cycloalkyl, heterocycle, hetrocycle$(C_1$-$C_8)$alkylene-, aryl, aryl$(C_1$-$C_8)$alkylene-, heteroaryl, heteroaryl$(C_1$-$C_8)$alkylene-, —$CO_2R^a$, $R^aC$(=O)O—, $R^aC$(=O), —$OCO_2R^a$, $R^bR^cNC$(=O)O—, $R^aOC$(=O)N($R^b$)—, $R^bR^cN$—, $R^bR^cNC$(=O)—, $R^aC$(=O)N($R^b$)—, $R^bR^cNC$(=O)N($R^b$)—, $R^bR^cNC$(=S)N($R^b$)—, —$OPO_3R^a$, $R^aOC$(=S)—, $R^aC$(=S)—, —$SSR^a$, $R^aS$(=O)—, $R^aS$(=O)$_2$—, —N=$NR^b$, or —$OPO_2R^a$;

each $R^2$ is independently hydrogen, halo, $(C_1$-$C_8)$alkyl, $(C_3$-$C_8)$cycloalkyl, heterocycle, heterocycle$(C_1$-$C_8)$ alkylene-, aryl, aryl$(C_1$-$C_8)$alkylene-, heteroaryl, or heteroaryl$(C_1$-$C_8)$alkylene-; or $R^1$ and $R^2$ and the atom to which they are attached is C=O, C=S or C=$NR^d$, $R^4$ and $R^5$ together with the atoms to which they are attached form a saturated or partially unsaturated, mono-, bicyclic- or aromatic ring having 3, 4, 5, 6, 7, 8, 9 or 10 ring atoms optionally comprising 1, 2, 3, or 4 heteroatoms selected from non-peroxide oxy (—O—), thio (—S—), sulfinyl (—SO—), sulfonyl (—S(O)$_2$—) or amine (—$NR^b$—) in the ring;

wherein any ring comprising $R^4$ and $R^5$ is substituted with from 0 to 14 $R^6$ groups; wherein each $R^6$ is independently halo, —OR —$SR^a$, $(C_1$-$C_8)$alkyl, cyano, nitro, trifluoromethyl, trifluoromethoxy, $(C_1$-$C_8)$cycloalkyl, $(C_6$-$C_{12})$bicycloalkyl, heterocycle or hetrocycle $(C_1$-$C_8)$alkylene-, aryl, aryl $(C_1$-$C_8)$alkylene-, heteroaryl, heteroaryl$(C_1$-$C_8)$alkylene-, —$CO_2R^a$, $R^aC$(=O)O—, $R^aC$(=O)—, —$OCO_2R^a$, $R^bR^cNC$(=O)O—, $R^aOC$(=O)N($R^b$)—, $R^bR^cN$—, $R^bR^cNC$(=O)—, $R^aC$(=O)N($R^b$)—, $R^bR^cNC$(=O)N ($R^b$)—, $R^bR^cNC$(=S)N($R^b$)—, —$OPO_3R^a$, $R^aOC$(=S)—, $R^aC$(=S)—, —$SSR^a$, $R^aS$(=O)—, —$NNR^b$,—$OPO_2R^a$, or two $R^6$ groups and the atom to which they are attached is C=O, C=S or; two $R^6$ groups together with the atom or atoms to which they are attached can form a carbocyclic or heterocyclic ring;

$R^3$ is hydrogen, halo, —$OR^a$, —$SR^a$, $(C_1$-$C_8)$alkyl, cyano, nitro, trifluoromethyl, trifluoromethoxy, $(C_3$-$C_8)$cycloalkyl, heterocycle, heterocycle$(C_1$-$C_8)$alkylene-, aryl, aryl$(C_1$-$C_8)$ alkylene-, heteroaryl, heteroaryl$(C_1$-$C_8)$alkylene-, —$CO_2R^a$, $R^aC$(=O)O—, $R^aC$(=O)—, —$OCO_2R^a$, $R^bR^cNC$(=O )O—, $R^aOC$(=O)N($R^b$)—, $R^bR^cN$—, $R^bR^cNC$(=O)—, $R^aC$(=O)N($R^b$), $R^bR^cNC$(=O)N($R^b$)—, $R^bR^cNC$(=S)N ($R^b$)—, —$OPO_3R^a$, $R^aOC$(=S)—, $R^aC$(=S)—, —$SSR^a$, $R^aS$(=O)—, $R^aS$(=O)$_2$—, —$NNR^b$, —$OPO_2R^a$; or if the ring formed from $CR^4R^5$ is aryl or hetreroaryl or partially unsaturated then $R^3$ can be absent;

each $R^7$ is independently hydrogen, $(C_1$-$C_8)$alkyl, $(C_3$-$C_8)$ cycloalkyl, aryl or aryl$(C_1$-$C_8)$alkylene, heteroaryl, heteroaryl$(C_1$-$C_8)$alkylene-;

X is —$CH_2OR^a$, —$CO_2R^a$, —$OC(O)R^a$, —$CH_2OC(O)R^a$, $C(O)NR^bR^c$, —$CH_2SR^a$, —$C(S)OR^a$, —$OC(S)R^a$, —$CH_2OC(S)R^a$ or —$C(S)NR^bR^c$ or —$CH_2N(R^b)(R^c)$;

wherein any of the alkyl, cycloalkyl, heterocycle, aryl, or heteroaryl, groups of $R^1$, $R^2$, $R^3$, $R^6$ and $R^7$ is optionally substituted on carbon with one or more (e.g. 1, 2, 3, or 4) substituents selected from the group consisting of halo, —$OR^a$, —$SR^a$, $(C_1$-$C_8)$alkyl, cyano, nitro, trifluoromethyl, trifluoromethoxy, $(C_3$-$C_8)$cycloalkyl, $(C_6$-$C_{12})$bicycloalkyl, heterocycle or heterocycle$(C_1$-$C_8)$-alkylene-, aryl, aryloxy, aryl$(C_1$-$C_8)$alkylene-, heteroaryl, heteroaryl$(C_1$-$C_8)$-alkylene-, —$CO_2R^a$, $R^aC$(=O)O—, $R^aC$(=O)—, —$OCO_2R^a$, $R^bR^cNC$(=O)O—, $R^aOC$(=O)N($R^b$)—, $R^bR^cN$—, $R^bR^cNC$(=O)—, $R^aC$(=O)N($R^b$)—, $R^bR^cNC$(=O)N ($R^b$)—, $R^bR^cNC$(=S)N($R^b$)—, —$OPO_3R^a$, $R^aOC$(=S)—, $R^aC$(=S)—, —$SSR^a$, $R^aS$(=O)$_p$—, $R^bR^cNS(O)_p$—, N=$NR^b$, and —$OPO_2R^a$;

wherein any $(C_1$-$C_8)$alkyl, $(C_3$-$C_8)$cycloalkyl, $(C_6$-$C_{12})$bicycloalkyl, $(C_1$-$C_8)$alkoxy, $(C_1$-$C_8)$alkanoyl, $(C_1$-$C_8)$alkylene, or heterocycle, is optionally partially unsaturated;

each $R^a$, $R^b$ and $R^c$ is independently hydrogen, $(C_1$-$C_8)$ alkyl, or $(C_1$-$C_8)$alkyl substituted with 1-3 $(C_1$-$C_8)$alkoxy, $(C_3$-$C_8)$cycloalkyl, $(C_1$-$C_8)$alkylthio, amino acid, aryl, aryl $(C_1$-$C_8)$alkylene, heteroaryl, or heteroaryl$(C_1$-$C_8)$alkylene; or $R^b$ and $R^c$, together with the nitrogen to which they are attached, form a pyrrolidino, piperidino, morpholino, or thiomorpholino ring; and $R^d$ is hydrogen or $(C_1$-$C_6)$alkyl; m is 0 to about 8 and p is 0 to 2; or a pharmaceutically acceptable salt thereof.

In another embodiment, the invention includes the use of compounds of formula (I) provided that m is at least 1 when Z is $NR^4R^5$.

Specific and preferred values listed below for radicals, substituents, and ranges, are for illustration only; they do not exclude other defined values or other values within defined ranges for the radicals and substituents.

A specific value for $R^1$ is hydrogen, —OH, —$CH_2OH$, —OMe, —OAc, —$NH_2$, —NHMe, —NMe$_2$ or —NHAc.

Another specific value for $R^1$ is hydrogen, —OH, —OMe, —OAc, —$NH_2$, —NHMe, —NMe$_2$ or —NHAc.

Another specific value for $R^1$ is hydrogen, —OH, —OMe, or —NH$_2$.

Another specific value for $R^1$ is hydrogen, —OH, or —NH$^2$.

A more specific value for $R^1$ is hydrogen or —OH.

A specific value for $R^1$, $R^2$ and the carbon atom to which they are attached is carbonyl (C=O).

A specific value for $R^2$ is hydrogen or (C$_1$-C$_8$)alkyl, cyclopropyl, cyclohexyl or benzyl.

Another specific value for $R^2$ is hydrogen, methyl, ethyl or propyl.

Another specific value for $R^2$ is hydrogen or methyl.

A more specific value for $R^2$ is hydrogen.

A specific value for $R^3$ is hydrogen, OH, OMe, OAc, NH$_2$, NHMe, NMe$_2$ or NHAc.

Another specific value for $R^3$ is hydrogen, OH, OMe, or NH$_2$.

Another specific value for $R^3$ is hydrogen, OH, or NH$_2$.

A more specific value for $R^3$ is hydrogen or OH.

A specific value for the ring comprising $R^4$, $R^5$ and the atom to which they are connected is cyclopentane, cyclohexane, piperidine, dihydro-pyridine, tetrahydro-pyridine, pyridine, piperazine, decaline, tetrahydro-pyrazine, dihydro-pyrazine, pyrazine, dihydro-pyrimidine, tetrahydro-pyrimidine, hexahydro-pyrimidine, pyrazine, imidazole, dihydro-imidazole, imidazolidine, pyrazole, dihydro-pyrazole, and pyrazolidine.

A more specific value for the ring comprising $R^4$ and $R^5$ and the atom to which they are connected is, cyclohexane, piperidine or piperazine.

A specific value for $R^6$ is (C$_1$-C$_8$)alkyl, or substituted (C$_1$-C$_8$)alkyl, —OR$^a$, —CO$_2$R$^a$, R$^a$C(=O)—, R$^a$C(=O)O—, R$^b$R$^c$N—, R$^b$R$^c$NC(=O)—, or aryl.

Another specific value for $R^6$ is (C$_1$-C$_8$)alkyl, —OR$^a$, —CO$_2$R$^a$, R$^a$C(=O)—, R$^a$C(=O)O—, R$^b$R$^c$N—, R$^b$R$^c$NC(=O)—, or aryl.

Another specific value for $R^6$ is methyl, ethyl, butyl, OH, OR$^a$, —CO$_2$R$^a$, R$^a$C(=O)—, OC(=O)CH$_2$CH$_3$, —CONR$^b$R$^c$, —NR$^b$R$^c$ or phenyl.

Another specific value for $R^6$ is OH, OMe, methyl, ethyl, t-butyl, CO$_2$R$^a$, —C(=O)NR$^b$R$^c$, —OAc, —NH$_2$, —NHMe, —NMe$_2$, —NHEt or —N(Et)$_2$.

Another specific value for $R^6$ is-(CH$_2$)$_{1-2}$OR$^a$, —(CH$_2$)$_{1-2}$C(=O)OR$^a$, —(CH$_2$)$_{1-2}$OC(=O)R$^a$, —(CH$_2$)$_{1-2}$C(=O)R$^a$, —(CH$_2$)$_{1-2}$OCO$_2$R$^a$, —(CH$_2$)$_{1-2}$NHR$^a$, —(CH$_2$)$_{1-2}$NR$^b$R$^c$, —(CH$_2$)$_{1-2}$OC(=O)NHR$^a$, or —CH$_2$)$_{1-2}$OC(=O)NR$^b$R$^c$.

Another specific value for $R^6$ is —CH$_2$OH, —CH$_2$OAc, —CH$_2$OCH$_3$, —CH$_2$C(=O)OCH$_3$, —CH$_2$PC(=O)CH$_3$, —CH$_2$C(=O)CH$_3$, —CH$_2$OCO$_2$CH$_3$, —CH$_2$NH(CH$_3$), or —(CH$_2$)$_{1-2}$N(CH$_3$)$_2$.

Another specific value for $R^6$ is methyl, ethyl, t-butyl, phenyl, —CO$_2$R$^a$, —CONR$^b$R$^c$, or R$^a$C(=O)—.

Another specific value for $R^6$ is —CH$_2$OH, —CH$_2$OAc, —C(=O)OCH$_3$, —C(=O)CH$_3$, OCO$_2$CH$_3$ —OCO$_2$CH$_3$, —CH$_2$NH(CH$_3$), or —(CH$_2$)$_{1-2}$N(CH$_3$)$_2$.

A more specific value for $R^6$ is methyl, ethyl, —CO$_2$R$^a$— CONR$^b$R$^c$, or R$^a$C(=O)—.

A specific number of $R^6$ groups substituted on the $R^4R^5$ ring is from 1 to about 4.

Specific values for $R^a$ and $R^b$ are independently hydrogen, (C$_1$-C$_4$)alkyl, aryl or aryl(C$_1$-C$_8$)alkylene.

More specific values for $R^a$ and $R^b$ are independently hydrogen, methyl, ethyl, phenyl or benzyl.

A more specific value for $R^a$ is (C$_1$-C$_8$)alkyl.

Another specific value for $R^a$ is methyl, ethyl, propyl or butyl.

A more specific value for $R^a$ is methyl, ethyl, i-propyl, i-butyl or tert-butyl.

Another specific value for $R^b$ and $R^c$ is a ring

A specific value for $R^7$ is hydrogen, alkyl, aryl or aryl(C$_1$-C$_8$)alkylene.

Another specific value for $R^7$ is hydrogen, methyl or ethyl, phenyl or benzyl.

A more specific value for $R^7$ is H, or methyl.

A specific value for —N(R$^7$)$_2$ is amino, methylamino, dimethylamino, ethylamino, pentylamino, diphenylethylamino, pyridylmethylamino (—NR—CH$_2$-Pyr, where R is a suitable group as described herein), diethylamino or benzylamino.

A specific value for —N(R$^7$)$_2$ is amino, methylamino, dimethylamino, ethylamino, diethylamino diphenylethylamino, pentylamino or benzylamino.

A specific value for N(R$^7$)$_2$ is amino, or methylamino.

A specific value for X is —CH$_2$OR$^a$, —CO$_2$R$^a$, —OC(O)R$^a$, -CH$_2$OC(O)R$^a$, —C(O)NR$^b$R$^c$.

Another specific value for X is —CH$_2$OR$^a$ or —C(O)NR$^b$R$^c$.

A more specific value for X is —CH$_2$OH or —C(O)NHCH$_2$CH$_3$.

A specific value for m is 0, 1, or 2.

A more specific value for m is 0, or 1.

Specific examples of rings comprising $R^4$, $R^5$ and the atom to which they are connected include:

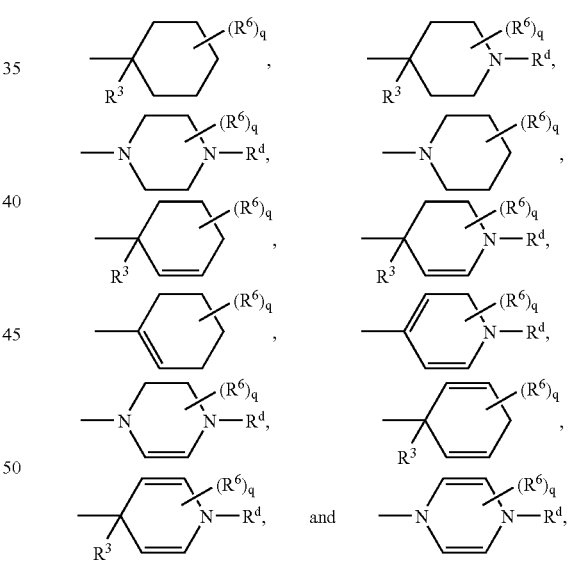

where q is from 0 to 14 and $R^d$ is hydrogen or $R^6$, provided that when q is zero then $R^d$ is not hydrogen.

More specific examples of rings comprising $R^4$, $R^5$ and the atom to which they are connected include:

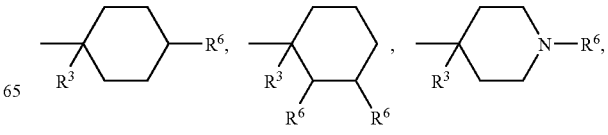

carboxylic acid tert-butyl ester 4-piperidine, 4-piperazine-1-carboxylic acid methyl ester, 4-piperidine-1-carboxylic acid tert-butylester, 1-piperidine-4-carboxylic acid methyl ester, 1-piperidine-4-caboxylic acid tert-butyl ester, tert-butylester, 1-piperidine-4-carboxylic acid methyl ester, or 1-piperidine-4-caboxylic acid tert-butyl ester, 3-piperidine-1-carboxylic acid methyl ester, 3-piperidine-1-carboxylic acid tert-butyl ester, 3-piperidine, 3-piperazine-1-carboxylic acid methyl ester, 3-piperidine-1-carboxylic acid tert-butylester, 1-piperidine-3-carboxylic acid methyl ester, 1-piperidine-3-caboxylic acid tert-butyl ester Specific compounds of formula (I) are those wherein each $R^7$ is H, X is ethylaminocarbonyl and $R^1$ is hydroxy, $R^2$ is hydrogen, and Z is 4-carboxycyclohexyl, wherein $R^a$ is hydrogen, 4; Z is 4-methoxycarbonylcyclohexylmethyl, $R^a$ is methyl, 5; $R^1$ and $R^2$ together are oxo, Z is a 4-carbonylcyclohexyl group, wherein $R^a$ is methyl, methoxy, ethyl, ethoxy, propyl, isopropoxy, -isobutyl, tert-butyl, amine, methylamine or dimethylamine, 6.

Specific values for the ring comprising $R^4$, $R^5$ and the atom to which they are connected are 2-methyl cyclohexane, 2,2-dimethylcyclohexane, 2-phenylcyclohexane, 2-ethylcyclohexane, 2,2-diethylcyclohexane, 2-tert-butyl cyclohexane, 3-methyl cyclohexane, 3,3-dimethylcyclohexane, 4-methyl cyclohexane, 4-ethylcyclohexane, 4-phenyl cyclohexane, 4-tert-butyl cyclohexane, 4-carboxymethyl cyclohexane, 4-carboxyethyl cyclohexane, 3,3,5,5-tetramethyl cyclohexane, 2,4-dimethyl cyclopentane. 4-cyclohexanecarboxyic acid, 4-cyclohexanecarboxyic acid esters, or 4-methyloxyalkanoyl-cyclohexane.

More specific values for the ring comprising $R^4$, $R^5$ and the atom to which they are connected are 4-piperidine, 4-piperidene-1-carboxylic acid, 4-piperidine-1-carboxylic acid methyl ester, 4-piperidine-1-carboxylic acid ethyl ester, 4-piperidine-1-carboxylic acid propyl ester, 4-piperidine-1-carboxylic acid tert-butyl ester, 1-piperidine, 1-piperidine-4-carboxylic acid methyl ester, 1-piperidine-4-carboxylic acid ethyl ester, 1-piperidine-4-carboxylic acid propyl ester, 1-piperidine-4-caboxylic acid tert-butyl ester, 1-piperidine-4-carboxylic acid methyl ester, 3-piperidine, 3-piperidene-1-carboxylic acid, 3-piperidine-1-carboxylic acid methyl ester, 3-piperidine-1-carboxylic acid tert-butyl ester, 1,4-piperazine, 4-piperazine-1-carboxylic acid, 4-piperazine-1-carboxylic acid methyl ester, 4-piperazine-1-carboxylic acid ethyl ester, 4-piperazine-1-carboxylic acid propyl ester, 4-piperazine-1-carboxylic acid tert-butylester, 1,3-piperazine, 3-piperazine-1-carboxylic acid, 3-piperazine-1-carboxylic acid methyl ester, 3-piperazine-1-carboxylic acid ethyl ester, 3-piperazine-1-carboxylic acid propyl ester, 3-piperidine-1-carboxylic acid tert-butylester, 1-piperidine-3-carboxylic acid methyl ester, 1-piperidine-3-carboxylic acid ethyl ester, 1-piperidine-3-carboxylic acid propyl ester or 1-piperidine-3-caboxylic acid tert-butyl ester.

Another group of specific values for the ring comprising $R^4$ and $R^5$ are 2-methyl cyclohexane, 2,2-dimethylcyclohexane, 2-phenyl cyclohexane, 2-ethylcyclohexane, 2,2-diethylcyclohexane, 2-tert-butyl cyclohexane, 3-methyl cyclohexane, 3,3-dimethylcyclohexane, 4-methyl cyclohexane, 4-ethylcyclohexane, 4-phenyl cyclohexane, 4-tert-butyl cyclohexane, 4-carboxymethyl cyclohexane, 4-carboxyethyl cyclohexane, 3,3,5,5-tetramethyl cyclohexane, 2,4-dimethyl cyclopentane, 4-piperidine-1-carboxylic acid methyl ester, 4-piperidine-1-

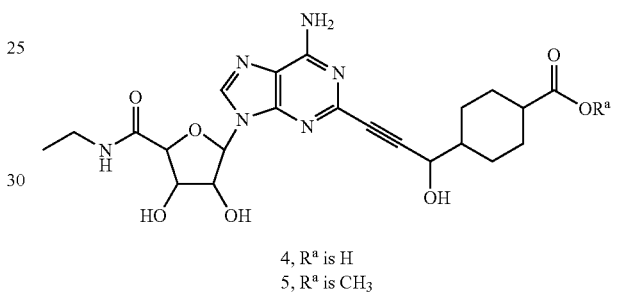

4, $R^a$ is H
5, $R^a$ is $CH_3$

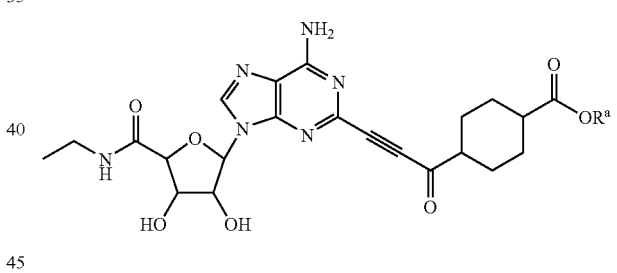

6

Another group of specific compounds of formula (I) are those wherein each $R^7$ is H, X is ethylaminocarbonyl, $R^1$ is hydroxy, $R^2$ is hydrogen, and Z is a substituted 4-(methyleneoxycarbonyl)cyclohexyl group, wherein $R^a$ is methyl, ethyl, propyl, tert-butyl, methoxy, ethoxy, methylamine or dimethylamine, 7; or $R^1$ and $R^2$ together are oxo, and Z is a substituted -(methyleneoxycarbonyl)-cyclohexyl group, wherein $R^a$ is methyl, ethyl, propyl, tert-butyl, methoxy, ethoxy, methylamine or dimethylamine, 8.

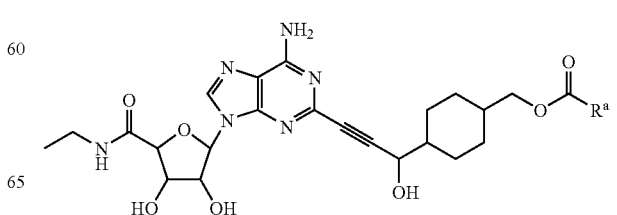

7

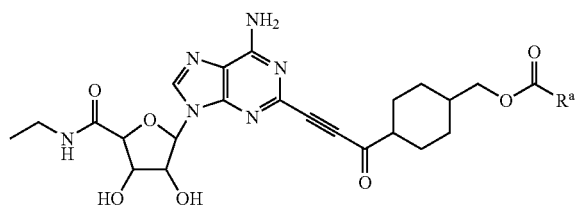

8

Another group of specific compounds of formula (I) are those wherein each $R^7$ is H, X is ethylaminocarbonyl, and $R^1$ and $R^2$ are each hydrogen, and Z is a 1-piperidyl-4-carboxylic acid or ester group, wherein $R^a$ is hydrogen, methyl, ethyl, propyl, isopropyl, or t-butyl, 9; $R^1$ and $R^2$ together are oxo, and Z is a 1-piperidyl-4-carboxylic acid or ester group, wherein $R^a$ is hydrogen, methyl, ethyl, propyl, isopropyl, or t-butyl, 10; $R^1$ and $R^2$ are each hydrogen and Z is a 4-(methyleneoxycarbonyl)piperidin-4-yl group wherein $R^a$ is methyl, ethyl, propyl or t-butyl, amine, methylamine, dimethylamine, 11; or $R^1$ and $R^2$ together are oxo, and Z is a 4-(methyleneoxycarbonyl)piperidin-4-yl wherein $R^a$ is methyl, ethyl, propyl or t-butyl, amine, methylamine, dimethylamine, 12; $R^1$ and $R^2$ are each hydrogen and Z is a 4-(methyleneoxycarbonyl)piperidin-4-yl-oxy wherein $R^a$ is hydrogen, methyl, ethy, propyl isopropyl, isobutyl, or t-butyl, 13 or $R^1$ and $R^2$ together are oxo, Z is a 4-(metheneoxycarbonyl)piperidin-4-yl-oxy wherein $R^a$ is hydrogen, methyl, ethyl, propyl, isopropyl, isobutyl, or t-butyl, 14.

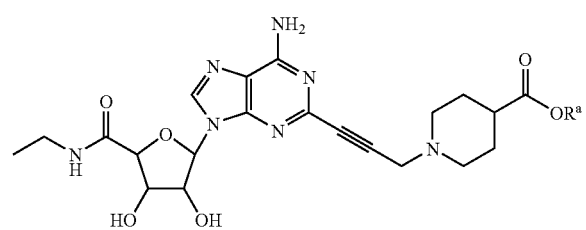

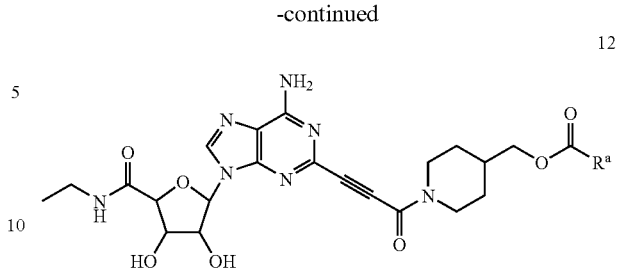

Another group of specific compounds of formula (I) are those wherein each $R^7$ is H, X is ethylaminocarbonyl, $R^1$ and $R^2$ are each hydrogen, and Z is a 4-piperidyl-1-carboxylic acid or ester group, wherein $R^a$ is methyl, ethyl, propyl, isopropyl, isobutyl, or t-butyl, 15, $R^1$ is hydroxy, $R^2$ is hydrogen, and Z is a 4-piperidyl-1-carboxylic acid or ester group, wherein $R^a$ is methyl, ethyl, propyl, isopropyl, isobutyl, or t-butyl, 16; or $R^1$ and $R^2$ together are oxo, and Z is a 4-piperidyl-1-carboxylic acid or ester group, wherein $R^a$ is methyl, ethyl, propyl, isopropyl, isobutyl, or t-butyl, 17.

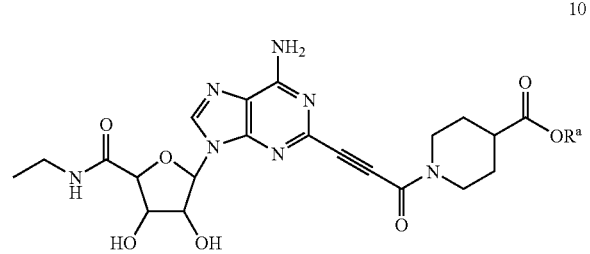

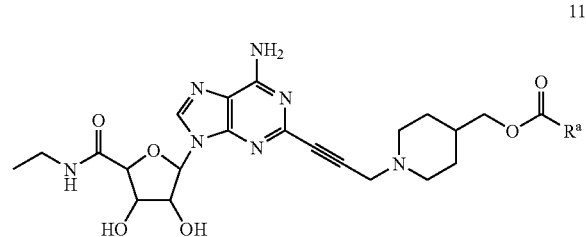

-continued

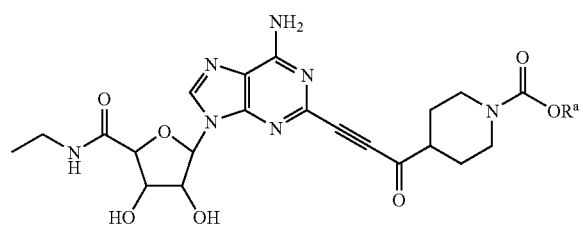
17

Another group of specific compounds of formula (I) are those wherein each R7 is H, X is ethylaminocarbonyl, R1 and R2 are each hydrogen, Z is a 4-piperazine-1-carboxylic acid or ester group wherein R$^a$ is methyl, ethyl, isopropyl, isobutyl, or t-butyl, 18; or R1 and R2 together are oxo, Z is a 4-piperazine-1-carboxylic acid or ester group wherein R$^a$ is methyl, ethyl, isopropyl, isobutyl, or t-butyl, 19.

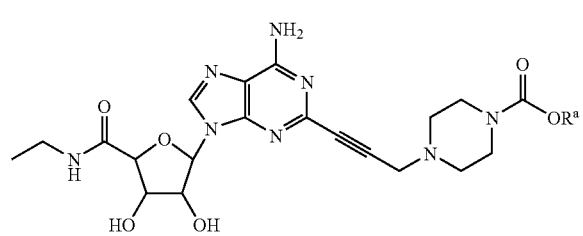
18

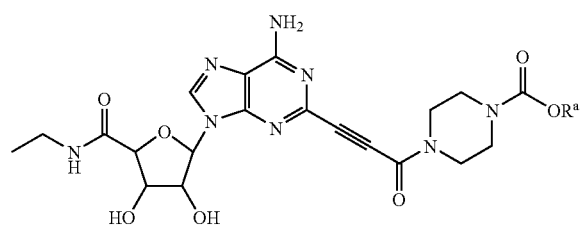
19

Additional compounds useful to practice the invention are depicted in tables 1, 2, 3, 4, 5, 6 and 7 below:

TABLE 1

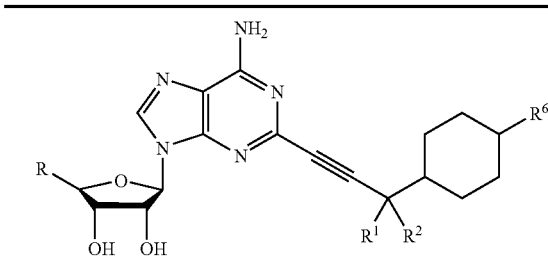

| Compound | R | R$^1$ | R$^2$ | R$^6$ |
|---|---|---|---|---|
| ATL2037 | NECA | H | H | CH$_2$OH |
| MP9056 | NECA | OH | H | CH$_2$OH |
| ATL146a | NECA | H | H | CO$_2$H |
| MP9057 | NECA | OH | H | CO$_2$H |
| ATL146e | NECA | H | H | CO$_2$Me |
| MP9058 | NECA | OH | H | CO$_2$Me |
| JR2145 | CH$_2$OH | H | H | CO$_2$Me |
| MP9059 | CH$_2$OH | OH | H | CO$_2$Me |
| ATL193 | NECA | H | H | CH$_2$OAc |
| MP9060 | NECA | OH | H | CH$_2$Oac |
| JR2147 | CH$_2$OH | H | H | CH$_2$Oac |
| MP9061 | CH$_2$OH | OH | H | CH$_2$Oac |
| JR3023 | NECA | H | H | CH$_2$N(CH$_3$)$_2$ |
| MP9062 | NECA | OH | H | CH$_2$N(CH$_3$)$_2$ |
| JR3021 | NECA | H | H | COOCH$_2$CH$_2$NHBoc |
| MP9063 | NECA | OH | H | COOCH$_2$CH$_2$NHBoc |
| JR3033 | NECA | H | H | COOCH$_2$CH$_2$NH$_2$ |
| MP9064 | NECA | OH | H | COOCH$_2$CH$_2$NH$_2$ |
| JR3037 | NECA | H | H | CONHCH$_2$CH$_3$ |
| MP9065 | NECA | OH | H | CONHCH$_2$CH$_3$ |
| JR3055 | NECA | H | H | CONH$_2$ |
| MP9072 | NECA | OH | H | CONH$_2$ |
| JR3065 | NECA | H | H | CONHMe |
| MP9066 | NECA | OH | H | CONHMe |
| JR3067B | NECA | H | H | Me, cis CO$_2$Me |
| MP9067 | NECA | OH | H | Me, cis CO$_2$Me |
| JR3067A | NECA | H | H | Me, trans CO$_2$Me |
| MP9068 | NECA | OH | H | Me, trans CO$_2$Me |
| JR3087 | NECA | H | H | CH$_2$CH$_3$ |
| MP9069 | NECA | OH | H | CH$_2$CH$_3$ |
| JR3159A | NECA | OH | H | H |
| JR3159B | NECA | OH | H | H |
| JR3119 | NECA | H | H | COCH$_3$ |
| MP9070 | NECA | OH | H | COCH$_3$ |
| JR3121 | NECA | H | H | CHCH$_3$(OH) |
| MP9071 | NECA | OH | H | CHCH$_3$(OH) |
| JR3139 | NECA | OH | C$_6$H$_{11}$ | H |

NECA = CH$_3$CH$_2$N(H)C(O)—

TABLE 2

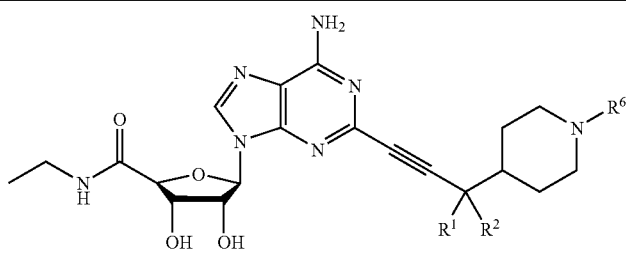

| Compound | R$^1$ | R$^2$ | R$^6$ |
|---|---|---|---|
| JR3261 | H | H | H |
| JR3259 | H | H | CO$_2$tBu |
| JR3269 | H | H | CO$_2$Et |
| JR4011 | H | H | CO$_2$iBu |
| JR4009 | H | H | CO$_2$iPr |

TABLE 2-continued

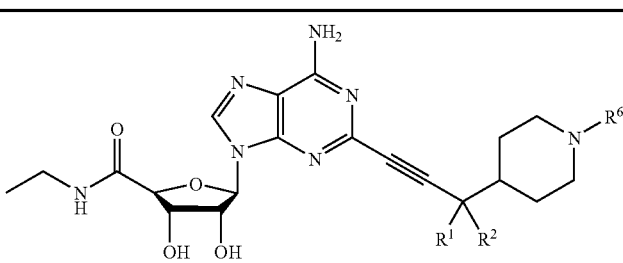

| Compound | R¹ | R² | R⁶ |
|---|---|---|---|
| JR4007 | H | H | COMe |
| JR4051 | H | H | COC(CH₃)₃ |
| JR4047 | H | H | COCH₂(CH₃)₃ |
| MP9047 | H | H | COCH₃ |
| MP9048 | H | H | C(O)N(CH₃)₂ |
| MP9049 | H | H | C(O)N(CH₃)Et |
| MP9050 | H | H | C(O)N(CH₃)iPr |
| MP9051 | H | H | C(O)N(CH₃)iBu |
| MP9052 | H | H | C(O)NH(CH₃) |
| MP9053 | H | H | C(O)NH(Et) |
| MP9054 | H | H | C(O)NH(iPr) |
| MP9055 | H | H | C(O)NH(iBu) |
| TX3261 | OH | H | H |
| TX3259 | OH | H | CO₂tBu |
| TX3269 | OH | H | CO₂Et |
| TX4011 | OH | H | CO₂iBu |
| TX4009 | OH | H | CO₂iPr |
| TX4007 | OH | H | COMe |
| TX4051 | OH | H | COC(CH₃)₃ |
| TX4047 | OH | H | COCH₂(CH₃)₃ |
| TX9047 | OH | H | COCH₃ |
| TX9048 | OH | H | C(O)N(CH₃)₂ |
| TX9049 | OH | H | C(O)N(CH₃)Et |
| TX9050 | OH | H | C(O)N(CH₃)iPr |
| TX9051 | OH | H | C(O)N(CH₃)iBu |
| TX9052 | OH | H | C(O)NH(CH₃) |
| TX9053 | OH | H | C(O)NH(Et) |
| TX9054 | OH | H | C(O)NH(iPr) |
| TX9055 | OH | H | C(O)NH(iBu) |

TABLE 3

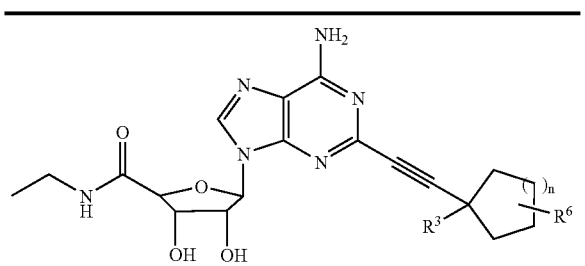

| Compound | n | R³ | R⁶ |
|---|---|---|---|
| JR3135 | 1 | OH | H |
| JR3089 | 2 | OH | H |
| JR3205 | 2 | NH₂ | H |
| JR3177A | 2 | OH | 2-CH₃ |
| JR3177B | 2 | OH | 2-CH₃ |
| JR3181A | 2 | OH | 2-CH₃ |
| JR3181B | 2 | OH | 2-CH₃ |
| JR3227 | 2 | OH | 2-C(CH₃)3 |
| JR9876 | 2 | OH | 2-C₆H₅ |
| JR3179 | 2 | OH | 3-CH₃ |
| JR3221 | 2 | OH (R) | 3-CH₃ (R) |
| ATL203 | 2 | OH (S) | 3-CH₃ (R) |
| MP9041 | 2 | OH (R) | 3-CH₃ (S) |
| MP9042 | 2 | OH (S) | 3-CH₃ (S) |

TABLE 3-continued

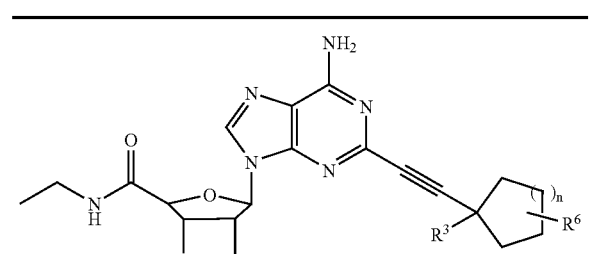

| Compound | n | R³ | R⁶ |
|---|---|---|---|
| JR3201B | 2 | OH | 3-(CH₃)₂ |
| MP9043 | 2 | OH (R) | 3-CH₂CH₃ (R) |
| MP9044 | 2 | OH (S) | 3-CH₂CH₃ (R) |
| MP9045 | 2 | OH (R) | 3-CH₂CH₃ (S) |
| MP9046 | 2 | OH (S) | 3-CH₂CH₃ (S) |
| JR3163 | 2 | OH | 3-(CH₃)₂, 5-(CH₃)₂ |
| JR9875 | 2 | OH | 4-CH₃ |
| JR3149 | 2 | OH | 4-C₂H₅ |
| JR3203 | 2 | OH | 4-C(CH₃)₃ |
| JR3161 | 2 | OH | 4-C₆H₅ |

TABLE 4

| Compound | R¹ | R² | R⁶ |
|---|---|---|---|
| JR3213 | H | H | CO$_2$Et |
| JR3281 | H | H | CO$_2$tBu |
| JR3289 | H | H | H |
| JR4025 | H | H | cyclohexyl |
| JR4053 | H | H | COMe |
| JR4049 | H | H | CO$_2$iBu |
| JR3283 | H | H | 2-Pyrimidinyl |
| MP9029 | H | H | COMe |
| MP9030 | H | H | COC(CH$_3$)$_3$ |
| MP9031 | H | H | COCH$_2$(CH$_3$)$_3$ |
| MP9032 | H | H | COCH$_3$ |
| MP9033 | H | H | C(O)N(CH$_3$)$_2$ |
| MP9034 | H | H | C(O)N(CH$_3$)Et |
| MP9035 | H | H | C(O)N(CH$_3$)iPr |
| MP9036 | H | H | C(O)N(CH$_3$)iBu |
| MP9037 | H | H | C(O)NH(CH$_3$) |
| MP9038 | H | H | C(O)NH(Et) |
| MP9039 | H | H | C(O)NH(iPr) |
| MP9040 | H | H | C(O)NH(iBu) |

TABLE 5

| Compound | R | R¹ | R² | R⁶ |
|---|---|---|---|---|
| MP9021 | NECA | H | H | CH$_2$OH |
| MP9022 | NECA | H | H | CO$_2$H |
| JR3251 | NECA | H | H | CO$_2$Me |
| JR3279 | NECA | H | H | CO$_2$Et |
| MP9027 | CH$_2$OH | H | H | CO$_2$Me |
| MP9028 | NECA | H | H | CO$_2$MeCH$_2$Ac |
| MP9015 | CH$_2$OH | H | H | CH$_2$OAc |
| MP9016 | NECA | H | H | CH$_2$N(CH$_3$)$_2$ |
| MP9017 | NECA | H | H | COOCH$_2$CH$_2$NHBoc |
| MP9018 | NECA | H | H | COOCH$_2$CH$_2$NH$_2$ |
| MP9019 | NECA | H | H | CONHCH$_2$CH$_3$ |
| MP9020 | NECA | H | H | CONH$_2$ |
| MP9023 | NECA | H | H | CONHMe |
| MP9024 | NECA | H | H | CH$_2$CH$_3$ |
| MP9025 | NECA | H | H | COCH$_3$ |
| MP9026 | NECA | H | H | CHCH$_3$(OH) |

NECA = CH$_3$CH$_2$N(H)C(O)—

TABLE 6

| Compound | R | R¹ | R² | R⁶ |
|---|---|---|---|---|
| MP9001 | NECA | H | H | CH$_2$OH |
| MP9002 | NECA | H | H | CO$_2$H |
| JR3253 | NECA | H | H | CO$_2$Me |
| MP9003 | CH$_2$OH | H | H | CO$_2$Me |
| MP9004 | NECA | H | H | CH$_2$OAc |
| MP9005 | CH$_2$OH | H | H | CH$_2$OAc |
| MP9006 | NECA | H | H | CH$_2$N(CH$_3$)$_2$ |
| MP9007 | NECA | H | H | COOCH$_2$CH$_2$NHBoc |
| MP9008 | NECA | H | H | COOCH$_2$CH$_2$NH2 |
| MP9009 | NECA | H | H | CONHCH$_2$CH$_3$ |
| MP9010 | NECA | H | H | CONH$_2$ |
| MP9011 | NECA | H | H | CONHMe |
| MP9012 | NECA | H | H | CH$_2$CH$_3$ |
| MP9013 | NECA | H | H | COCH$_3$ |
| MP9014 | NECA | H | H | CHCH$_3$(OH) |

NECA = CH$_3$CH$_2$N(H)C(O)—

TABLE 7

| Compound | R | Y | Y' | R⁶ |
|---|---|---|---|---|
| RJ1111 | NECA | CH | CH | CO₂Me |
| RJ1112 | NECA | CH | N | CO₂Me |
| RJ1113 | NECA | N | CH | CO₂Me |
| RJ1114 | NECA | N | N | CO₂Me |
| RJ1115 | NECA | CH | CH | CH₂OH |
| RJ1116 | NECA | CH | N | CH₂OH |
| RJ1117 | NECA | N | CH | CH₂OH |
| RJ1118 | NECA | N | N | CH₂OH |
| RJ1119 | NECA | CH | CH | CO₂H |
| RJ1120 | NECA | CH | N | CO₂H |
| RJ1121 | NECA | N | CH | CO₂H |
| RJ1122 | NECA | N | N | CO₂H |
| RJ1123 | NECA | CH | CH | CH₂OAc |
| RJ1124 | NECA | CH | N | CH₂OAc |
| RJ1125 | NECA | N | CH | CH₂OAc |
| RJ1126 | NECA | N | N | CH₂OAc |
| RJ1127 | NECA | CH | CH | CONH₂ |
| RJ1128 | NECA | CH | N | CONH₂ |
| RJ1129 | NECA | N | CH | CONH₂ |
| RJ1130 | NECA | N | N | CONH₂ |
| RJ1131 | NECA | CH | CH | CONHMe |
| RJ1132 | NECA | CH | N | CONHMe |
| RJ1133 | NECA | N | CH | CONHMe |
| RJ1134 | NECA | N | N | CONHMe |
| RJ1135 | NECA | CH | CH | CO₂tBu |
| RJ1136 | NECA | CH | N | CO₂tBu |
| RJ1137 | NECA | N | CH | CO₂tBu |
| RJ1138 | NECA | N | N | CO₂tBu |
| RJ1139 | NECA | CH | CH | CO₂Et |
| RJ1140 | NECA | CH | N | CO₂Et |
| RJ1141 | NECA | N | CH | CO₂Et |
| RJ1142 | NECA | N | N | CO₂Et |
| RJ1143 | NECA | CH | CH | CO₂iBu |
| RJ1144 | NECA | CH | N | CO₂iBu |
| RJ1145 | NECA | N | CH | CO₂iBu |
| RJ1146 | NECA | N | N | CO₂iBu |
| RJ1147 | NECA | CH | CH | CO₂iPr |
| RJ1148 | NECA | CH | N | CO₂iPr |
| RJ1149 | NECA | N | CH | CO₂iPr |
| RJ1150 | NECA | N | N | CO₂iPr |
| RJ1151 | NECA | CH | CH | COMe |
| RJ1152 | NECA | CH | N | COMe |
| RJ1153 | NECA | N | CH | COMe |
| RJ1154 | NECA | N | N | COMe |
| RJ1155 | NECA | CH | CH | COC(CH₃)₃ |
| RJ1156 | NECA | CH | N | COC(CH₃)₃ |
| RJ1157 | NECA | N | CH | COC(CH₃)₃ |
| RJ1158 | NECA | N | N | COC(CH₃)₃ |
| RJ1159 | NECA | CH | CH | COCH₂(CH₃)₃ |
| RJ1160 | NECA | CH | N | COCH₂(CH₃)₃ |
| RJ1161 | NECA | N | CH | COCH₂(CH₃)₃ |
| RJ1162 | NECA | N | N | COCH₂(CH₃)₃ |
| RJ1163 | NECA | CH | CH | C(O)N(CH₃)₂ |
| RJ1164 | NECA | CH | N | C(O)N(CH₃)₂ |
| RJ1165 | NECA | N | CH | C(O)N(CH₃)₂ |
| RJ1166 | NECA | N | N | C(O)N(CH₃)₂ |
| RJ1167 | NECA | CH | CH | C(O)N(CH₃)Et |
| RJ1168 | NECA | CH | N | C(O)N(CH₃)Et |
| RJ1169 | NECA | N | CH | C(O)N(CH₃)Et |
| RJ1170 | NECA | N | N | C(O)N(CH₃)Et |
| RJ1171 | NECA | CH | CH | C(O)N(CH₃)iPr |
| RJ1172 | NECA | CH | N | C(O)N(CH₃)iPr |
| RJ1173 | NECA | N | CH | C(O)N(CH₃)iPr |
| RJ1174 | NECA | N | N | C(O)N(CH₃)iPr |
| RJ1175 | NECA | CH | CH | C(O)N(CH₃)iBu |
| RJ1176 | NECA | CH | N | C(O)N(CH₃)iBu |
| RJ1177 | NECA | N | CH | C(O)N(CH₃)iBu |
| RJ1178 | NECA | N | N | C(O)N(CH₃)iBu |
| RJ1179 | NECA | CH | CH | C(O)NH(Et) |
| RJ1180 | NECA | CH | N | C(O)NH(Et) |
| RJ1181 | NECA | N | CH | C(O)NH(Et) |
| RJ1182 | NECA | N | N | C(O)NH(Et) |
| RJ1183 | NECA | CH | CH | C(O)NH(iPr) |
| RJ1184 | NECA | CH | N | C(O)NH(iPr) |
| RJ1185 | NECA | N | CH | C(O)NH(iPr) |
| RJ1186 | NECA | N | N | C(O)NH(iPr) |
| RJ1187 | NECA | CH | CH | C(O)NH(iBu) |
| RJ1188 | NECA | CH | N | C(O)NH(iBu) |
| RJ1189 | NECA | N | CH | C(O)NH(iBu) |
| RJ1190 | NECA | N | N | C(O)NH(iBu) |
| RJ1191 | NECA | CH | CH | CH₂OCOCH₃ |
| RJ1192 | NECA | N | CH | CH₂OCOCH₃ |
| RJ1193 | NECA | CH | CH | CH₂OCOEt |
| RJ1194 | NECA | N | CH | CH₂OCOEt |
| RJ1195 | NECA | CH | CH | CH₂OCOiPr |
| RJ1196 | NECA | N | CH | CH₂OCOiPr |
| RJ1197 | NECA | CH | CH | CH₂OCOiBu |
| RJ1198 | NECA | N | CH | CH₂OCOiBu |

NECA = CH₃CH₂N(H)C(O)—

In another embodiment, agonists of $A_{2A}$ adenosine receptors that are useful in the practice of the present invention include compounds having the formula (II):

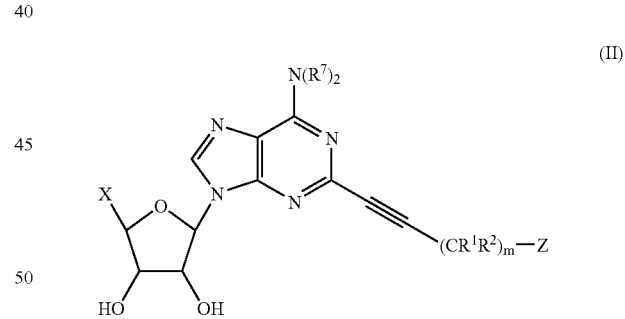

wherein Z is $CR^3R^4R^5$; each $R^1$, $R^2$ and $R^3$ is hydrogen; $R^4$ and $R^5$ together with the carbon atom to which they are attached form a cycloalkyl ring having 3, 4, 5, 6, 7, 8, 9 or 10 ring atoms; and wherein the ring comprising $R^4$ and $R^5$ is substituted with —(CH₂)₀₋₆—Y; where Y is —CH₂OR$^a$, —CO₂R$^a$, —OC(O)R$^a$, CH₂OC(O)R$^a$, C(O)NR$^b$R$^c$, —CH₂SR$^a$, —C(S)OR$^a$, —OC(S)R$^a$, —CH₂OC(S)R$^a$ or C(S)NR$^b$R$^c$ or —CH₂N(R$^b$)(R$^c$);

each $R^7$ is independently hydrogen, (C₁-C₈)alkyl, (C₃-C₈) cycloalkyl, aryl or aryl(C₁-C₈)alkylene;

X is —CH₂OR$^a$, —CO₂R$^a$, —OC(O)R$^a$, —CH₂OC(O)R$^a$, —C(O)NR$^b$R$^c$, —CH₂SR$^a$, —C(S)OR$^a$, —OC(S)R$^a$, —CH₂OC(S)R$^a$ or C(S)NR$^b$R$^c$ or —CH₂N(R$^b$)(R$^c$);

each $R^a$, $R^b$ and $R^c$ is independently hydrogen, $(C_1-C_8)$alkyl, or $(C_1-C_8)$alkyl substituted with 1-3 $(C_1-C_8)$alkoxy, $(C_3-C_8)$cycloalkyl, $(C_1-C_8)$alkylthio, amino acid, aryl, aryl$(C_1-C_8)$alkylene, heteroaryl, or heteroaryl$(C_1-C_8)$alkylene; or $R^b$ and $R^c$, together with the nitrogen to which they are attached, form a pyrrolidino, piperidino, morpholino, or thiomorpholino ring; and m is 0 to about 6; or a pharmaceutically acceptable salt thereof.

A specific value for $—N(R^7)_2$ is amino, monomethylamino or cyclopropylamino.

A specific value for Z is carboxy- or $—(C_1-C_4)$alkoxycarbonyl-cyclohexyl$(C_1-C_4)$alkyl.

A specific value for $R^a$ is H or $(C_1-C_4)$alkyl, i.e., methyl or ethyl.

A specific value for $R^b$ is H, methyl or phenyl.

A specific value for $R^c$ is H, methyl or phenyl.

A specific value for $—CR^1R^2)_m—$ is $—CH_2—$ or $—CH_2—CH_2—$.

A specific value for X is $CO_2R^a$, $(C_2-C_5)$alkanoylmethyl or amido.

A specific value for Y is $CO_2R^a$, $(C_2-C_5)$alkanoylmethyl or amido.

A specific value for m is 1.

Specific $A_{2A}$ adenosine receptor agonists suitable for use with the present invention having formula (II) include those described in U.S. Pat. No.: 6,232,297. Preferred compounds of formula (II) are those wherein each $R^7$ is H, X is ethylaminocarbonyl and Z is 4-carboxycyclohexylmethyl (ATL-146a), Z is 4-methoxycarbonylcyclohexylmethyl (ATL-146e), Z is 4-isopropylcarbonyl-cyclohexylmethyl (ATL-1), Z is 4-acetoxymethyl-cyclohexylmethyl (ATL-193) or Z is 4-pyrrolidine-1-carbonylcyclohexylmethyl (ATL-3). These compounds are depicted below.

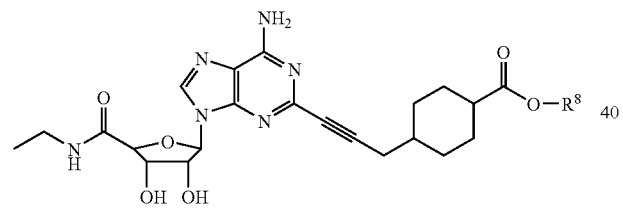

ATL-146: $R^8$ = H or Me.
ATL-1: $R^8$ = iPr

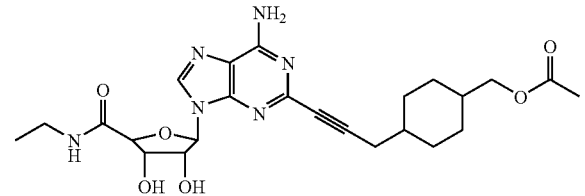

ATL-193

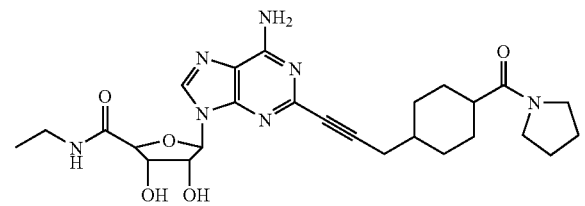

ATL-3

The specific $A_{2A}$ adenosine receptor agonists suitable for use with the present invention having formula (II) include those described in U.S. Pat. No. 6,232,297. These compounds, having formula (II), can be prepared according to the methods described therein.

Another specific group of agonists of $A_{2A}$ adenosine receptors that are useful in the practice of the present invention include compounds having the general formula (III):

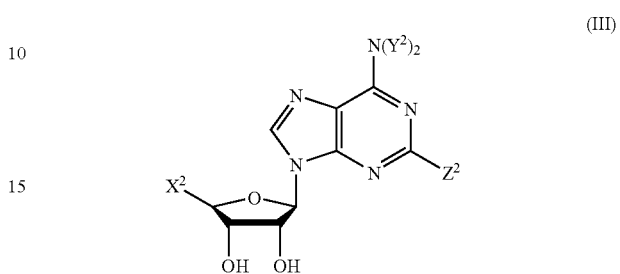

(III)

wherein $Z^2$ is a group selected from the group consisting of $—OR^{12}$, $—NR^{13}R^{14}$, a $—C\equiv C-Z^3$, and $—NH—N=R^{17}$;

each $Y^2$ is individually H, $(C_1-C_6)$alkyl, $(C_3-C_7)$cycloalkyl, phenyl or phenyl$(C_1-C_3)$alkyl;

$R^{12}$ is $(C_1-C_4)$alkyl; $C_{1-4}$-alkyl substituted with one or more $(C_1-C_4)$alkoxy groups, halogens (fluorine, chlorine or bromine), hydroxy groups, amino groups, mono$((C_1-C_4)$alkyl)amino groups, di$((C_1-C_4)$alkyl)amino groups or $(C_6-C_{10})$aryl groups wherein the aryl groups may be substituted with one or more halogens (fluorine, chlorine or bromine), $(C_1-C_4)$alkyl groups, hydroxy groups, amino groups, mono$((C_1-C_4)$alkyl)amino groups or di$((C_1-C_4)$alkyl)amino groups); $(C_6-C_{10})$aryl; or $C_{6-10}$-aryl substituted with one or more halogens (fluorine, chlorine or bromine), hydroxy groups, amino groups, mono$((C_1-C_4)$alkyl)amino groups, di$((C_1-C_4)$alkyl)amino groups or $(C_1-C_4)$alkyl groups; one of $R^{13}$ and $R^{14}$ has the same meaning as $R^{12}$ and the other is hydrogen; and $R^{17}$ is a group having the formula (i)

(i)

wherein each of $R^{15}$ and $R^{16}$ independently may be hydrogen, $(C_3-C_7)$cycloalkyl or any of the meanings of $R^{12}$, provided that $R^{15}$ and $R^{16}$ are not both hydrogen;

$X^2$ is $CH_2OH$, $CH_3$, $CO_2R^{20}$ or $C(=O)NR^{21}R^{22}$ wherein $R^{20}$ has the same meaning as $R^{13}$ and wherein $R^{21}$ and $R^{22}$ have the same meanings as $R^{15}$ and $R^{16}$ or $R^{21}$ and $R^{22}$ are both H;

$Z^3$ has one of the following meanings:

$(C_6-C_{10})$aryl, optionally substituted with one to three halogen atoms, $(C_1-C_6)$alkyl, $(C_1-C_6)$haloalkyl, $(C_1-C_6)$alkoxy, $(C_1-C_6)$haloalkoxy, $(C_2-C_6)$alkoxycarbonyl, $C_2-C_6$ alkoxyalkyl, $(C_1-C_6)$alkylthio, thio, CHO, cyanomethyl, nitro, cyano, hydroxy, carboxy, $(C_2-C_6)$acyl, amino $(C_1-C_3)$ monoalkylamino, $(C_2-C_6)$dialkylamino, methylenedioxy or aminocarbonyl;

a group of formula $—CH_2)_q$-Het wherein q is 0 or an integer from 1 to 3 and Het is 5 or 6 membered heterocyclic aromatic or non-aromatic ring, optionally benzocondensed, containing 1 to 3 heteroatoms selected from nonperoxide oxygen, nitrogen or sulphur, linked through a carbon atom or through a nitrogen atom;

($C_3$-$C_7$)cycloalkyl optionally containing unsaturation or ($C_2$-$C_4$)alkenyl;

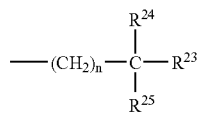 (ii)

wherein $R^{23}$ is hydrogen, methyl or phenyl;

$R^{24}$ is hydrogen, ($C_1$-$C_6$)linear or branched alkyl, ($C_5$-$C_6$) cycloalkyl or ($C_3$-$C_7$)cycloalkenyl, phenyl($C_1$-$C_2$)alkyl or $R^{23}$ and $R^{24}$, taken together, form a 5 or 6-membered carbocyclic ring or $R^{25}$ is hydrogen and $R^{23}$ and $R^{24}$, taken together, form an oxo group or a corresponding acetalic derivative;

$R^{25}$ is OH, $NH_2$ dialkylamino, halogen, cyano; and n is 0 or 1 to 4; or ($C_1$-$C_{16}$)alkyl, optionally comprising 1-2 double bonds, O, S or $NY^2$;

or a pharmaceutically acceptable salt thereof.

Specific ($C_6$-$C_{10}$)aryl groups include phenyl and naphthyl.

Preferably, in the compound of formula (I), $Z^2$ is a group of the formula (iii)

—O—($CH_2$)$_n$—Ar (iii)

wherein n is an integer from 1-4, preferably 2, and Ar is a phenyl group, tolyl group, naphthyl group, xylyl group or mesityl group. Most preferably Ar is a para-tolyl group and n=2.

Preferably, in the compound of formula (II), $Z^2$ is a group of the formula (iv)

—NH—N=CHCy (iv)

wherein Cy is a $C_{3-7}$-cycloalkyl group, preferably cyclohexyl or a ($C_1$-$C_4$)alkyl group, preferably isopropyl.

Preferably, in the compound of formula (II), $Z^2$ is a group of the formula (vii)

—C≡C-$Z^3$ (v)

wherein $Z^3$ is ($C_3$-$C_{16}$)alkyl, hydroxyl($C_2$-$C_6$)alkyl or (phenyl)-(hydroxymethyl).

Specific examples of such compounds of formula (I) include WRC-0470, WRC-0474 [SHA 211], WRC-0090, WRC-0094 and WRC-0018, shown below:

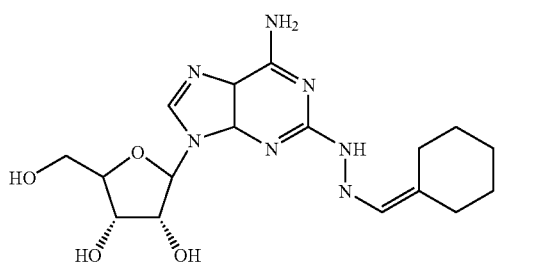
WRC-0470

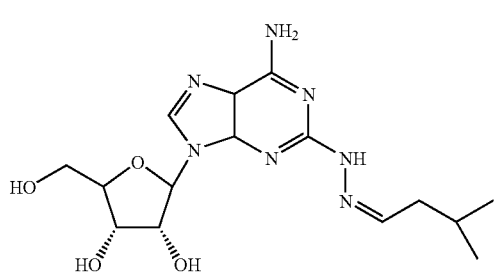
WRC-0474

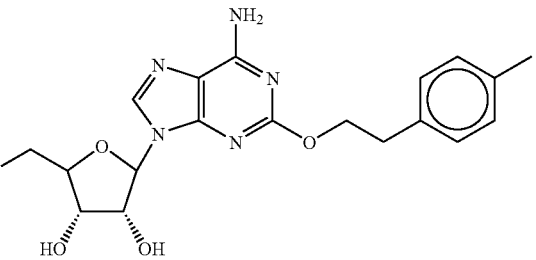
WRC-0090

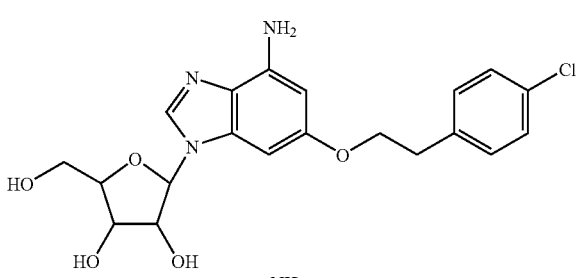
WRC-0094

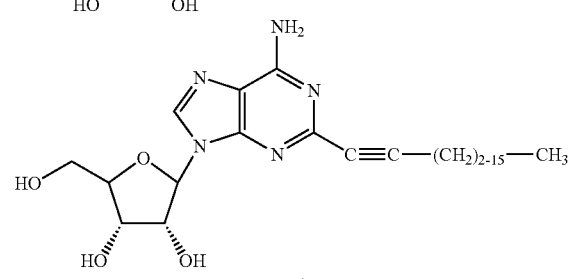

and

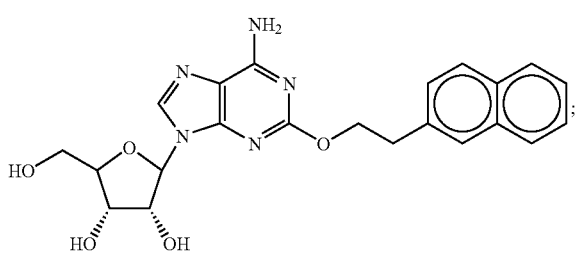
WRC-0018 wherein the H on the $CH_2OH$ group can optionally be replaced by ethylaminocarbonyl. Of these specific examples, WRC-0474[SHA 211] and WRC-0470 are particularly preferred.

Such compounds may be synthesized as described in: Olsson et al. (U.S. Pat. Nos. 5,140,015 and 5,278,150); Cristalli (U.S. Pat. No. 5,593,975); Miyasaka et al. (U.S. Pat. No. 4,956,345); Hutchinson, A. J. et al., *J. Pharmacol. Exp. Ther.*, 251, 47 (1989); Olsson, R. A. et al., *J. Med. Chem.*, 29, 1683 (1986); Bridges, A. J. et al., *J. Med. Chem.*, 31, 1282 (1988); Hutchinson, A. J. et al., *J. Med. Chem.*, 33, 1919 (1990); Ukeeda, M. et al., *J. Med. Chem.*, 34, 1334 (1991); Francis, J. E. et al., *J. Med. Chem.*, 34, 2570 (1991); Yoneyama, F. et al., *Eur. J. Pharmacol.*, 213, 199-204 (1992); Peet, N. P. et al., *J. Med. Chem.*, 35, 3263 (1992); and Cristalli, G. et al., *J. Med. Chem.*, 35, 2363 (1992); all of which are incorporated herein by reference.

Another embodiment includes compounds having formula (III) where $Z^2$ is a group having formula (vi):

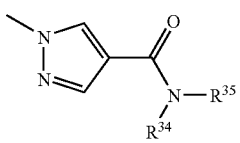

(vi)

wherein $R^{34}$ and $R^{35}$ are independently H, $(C_1-C_6)$alkyl, $(C_3-C_7)$cycloalkyl, phenyl, phenyl $(C_1-C_3)$alkyl or $R^{34}$ and $R^{35}$ taken together with the nitrogen atom are a 5- or 6-membered heterocyclic ring containing 1-2 heteroatoms selected from nonperoxide oxygen, nitrogen $(N(R^{13}))$ or sulphur atoms. Preferably one of $R^{34}$ and $R^{35}$ is hydrogen and the other is ethyl, methyl or propyl. More preferably one of $R^{34}$ and $R^{35}$ is hydrogen and the other is ethyl or methyl.

The 2-(pyrazol-1-yl)adenosine compounds of the invention, wherein $Z^2$ is a group having formula (vi), can be prepared by reacting a 2-chloro- or 2-iodo adenosine derivative with an 1H-pyrazole-4-carboxamides compound having formula (vii):

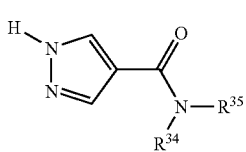

(vii)

where $R^{34}$ and $R^{35}$ are as described above, wherein selective protection/deprotection of the amido group is used as needed. A preferred pyrazole derivative useful in practicing this invention is a compound having the formula:

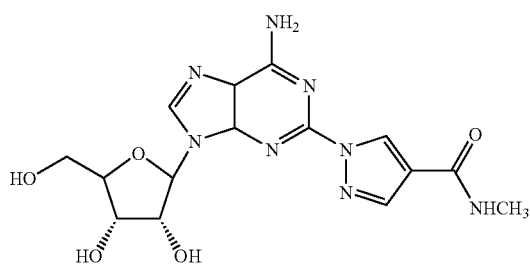

The 1 H-pyrazole-4-carboxamides can be prepared starting with 1H-pyrazole-4-carboxylic acid, available from Aldrich Chemical Co. In the first step, the acid is converted to an ester, e.g., a methyl or ethyl ester. The ester converted to the amide via aminolysis, e.g., with methylamine to form the methyl amide. The pyrazole-4-carboxamide will react with the 2-halopurines in the presence of a strong base to provide the 2-(pyrazol-1-yl)adenosine compounds having formula (III).

Another specific group of agonists of $A_{2A}$ adenosine receptors that are useful in the practice of the present invention include compounds having the general formula (IV):

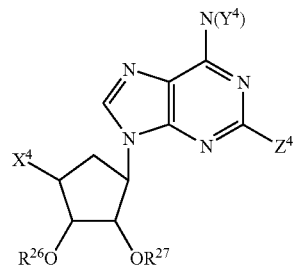

(IV)

wherein $Z^4$ is $-NR^{28}R^{29}$;

$R^{28}$ is hydrogen or $(C_1-C_4)$alkyl; and $R^{29}$ is a) $(C_1-C_4)$alkyl;

b) $(C_1-C_4)$alkyl substituted with one or more $(C_1-C_4)$ alkoxy, halogen, hydroxy, amino, mono$((C_1-C_4)$alkyl)amino, di$((C_1-C_4)$alkyl)amino or $(C_6-C_{10})$aryl wherein aryl is optionally substituted with one or more halogen, hydroxy, amino, $-(C_1-C_4)$alkyl, $R^{30}OOC-((C_1-C_4)$alkyl)-, $R^{31}R^{32}NC(=O)-((C_1-C_4)$alkyl)-, mono$((C_1-C_4)$alkyl)amino or di$((C_1-C_4)$alkyl)amino;

c) $-(C_6-C_{10})$aryl; or d) $-(C_6-C_{10})$aryl substituted with one or more halogen, hydroxy, amino, mono$((C_1-C_4)$alkyl)amino, di$((C_1-C_4)$alkyl)amino or $(C_1-C_4)$alkyl;

wherein each $Y^4$ is individually H, $(C_1-C_6)$alkyl, $(C_3-C_7)$cycloalkyl, phenyl or phenyl$(C_1-C_3)$alkyl; and $X^4$ is $-C(=O)NR^{31}R^{32}$, $-COOR^{30}$, or $-CH_2OR^{30}$;

wherein each of $R^{31}$ and $R^{32}$ are independently; hydrogen; $C_{3-7}$-cycloalkyl; $(C_1-C_4)$alkyl; $(C_1-C_4)$alkyl substituted with one or more $(C_1-C_4)$alkoxy, halogen, hydroxy, $-COOR^{33}$, amino, mono$((C_1-C_4)$alkyl)amino, di$((C_1-C_4)$alkyl)amino or $(C_6-C_{10})$aryl wherein aryl is optionally substituted with one or more halogen, $(C_1-C_4)$alkyl, hydroxy, amino, mono$((C_1-C_4)$alkyl)amino or di$((C_1-C_4)$ alkyl)amino; $(C_6-C_{10})$aryl; or $(C_6-C_{10})$aryl substituted with one or more halogen, hydroxy, amino, mono$((C_1-C_4)$alkyl)amino, di$((C_1-C_4)$alkyl)amino or $(C_1-C_4)$alkyl;

$R^{26}$ and $R^{27}$ independently represent hydrogen, lower alkanoyl, lower alkoxy-lower alkanoyl, aroyl, carbamoyl or mono- or di-lower alkylcarbamoyl; and $R^{30}$ and $R^{33}$ are independently hydrogen, $(C^1-C_4)$alkyl, $(C_6-C_{10})$aryl or $(C_6-C_{10})$ aryl$((C_1-C_4)$alkyl); or a pharmaceutically acceptable salt thereof.

In one embodiment of formula (IV), at least one of $R^{28}$ and $R^{29}$ is $(C_1-C_4)$alkyl substituted with one or more $(C_1-C_4)$ alkoxy, halogen, hydroxy, amino, mono$((C_1-C_4)$alkyl)amino, di$((C_1-C_4)$alkyl)amino or $(C_6-C_{10})$aryl wherein aryl is optionally substituted with one or more halogen, hydroxy, amino, $(C_1-C_4)$alkyl, $R^{30}OOC-(C_1-C_4)$alkyl, mono$((C_1-C_4)$alkyl)amino or di$((C_1-C_4)$alkyl)amino.

In another embodiment, at least one of $R^{31}$ and $R^{32}$ is $C_{1-4}$-alkyl substituted with one or more $(C_1-C_4)$alkoxy, halogen, hydroxy, amino, mono$((C_1-C_4)$alkyl)amino, di$((C_1-C_4)$ alkyl)amino or $C_{6-10}$-aryl wherein aryl is optionally substituted with one or more halogen, hydroxy, amino, $(C_1-C_4)$ alkyl, $R^{30}OOC$—$(C_1$-$C_4)$alkylene-, mono(($C_1$-$C_4$)alkyl) amino or di(($C_1$-$C_4$)alkyl)amino.

In another embodiment, at least one of $R^{28}$ and $R^{29}$ is $C_{6-10}$-aryl substituted with one or more halogen, hydroxy, amino, mono(($C_1$-$C_4$)alkyl)amino, di(($C_1$-$C_4$)alkyl)amino or ($C_1$-$C_4$)alkyl.

In another embodiment, at least one of $R^{31}$ and $R^{32}$ is $C_{6-10}$-aryl substituted with one or more halogen, hydroxy, amino, mono(($C_1$-$C_4$)alkyl)-amino, di(($C_1$-$C_4$)alkyl)amino or ($C_1$-$C_4$)alkyl.

In a preferred combination, $R^{31}$ is hydrogen and $R^{32}$ is ($C_1$-$C_4$)alkyl, cyclopropyl or hydroxy-($C_2$-$C_4$)alkyl. A preferred $R^{28}$ group is ($C_1$-$C_4$)alkyl substituted with ($C_6$-$C_{10}$) aryl, that is in turn substituted with $R^{30}O(O)C$—($C_1$-$C_4$)alkyline-.

A preferred compound having formula (IV) is:

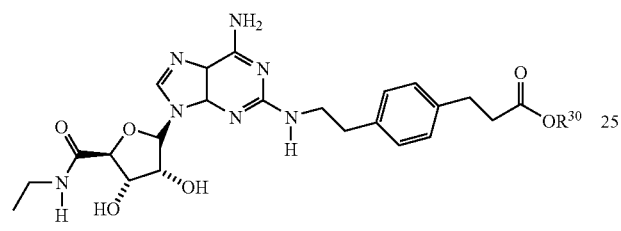

wherein $R^{30}$ is hydrogen, methyl, ethyl, n-propyl or iso-propyl. More preferred is a compound wherein the $R^{30}$ group is methyl or ethyl. The most preferred $R^{30}$ group is methyl.

Two compounds that are particularly useful in practicing the present invention have the formula:

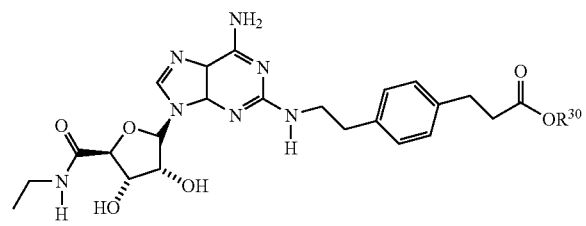

wherein $R^{30}$ is hydrogen (acid, CGS21680) and where $R^{30}$ is methyl (ester, JR2171).

The compounds of the invention having formula (IV) may be synthesized as described in: U.S. Pat. No. 4,968,697 or *J. Med. Chem.*, 33, 1919-1924, (1990)

Specifically, the invention also provides the use of a compound of formula (I) or a pharmaceutically acceptable salt thereof to prepare a medicament for treating systemic intoxification in a mammal (e.g. a human),.

Specifically, the invention also provides the use of a compound of formula (I) or a pharmaceutically acceptable salt thereof to prepare a medicament for treating inflammation caused by a diabetic condition such as, for example, as diabetic kidney disease, e.g., diabetic nephropathy in a mammal (e.g. a human).

The present method also includes the administration of a Type IV phosphodiesterase (PDE) inhibitor in combination with compounds having formulae (I), (II), (III), and (IV). The combination of the compounds of the invention with type IV phosphodiesterase inhibitor provides synergistic decreases in the inflammatory response of immune cells. Examples of Type IV phosphodiesterase (PDE) inhibitors include those disclosed in U.S. Pat. No. 4,193,926, and WO 92-079778, and Molnar-Kimber, K. L. et al., *J. Immunol.*, 150, 295A (1993), all of which are incorporated herein by reference.

Suitable Type IV phosphodiesterase (PDE) inhibitors include racemic and optically active 4-(polyalkoxyphenyl)-2-pyrrolidones of general formula (VI):

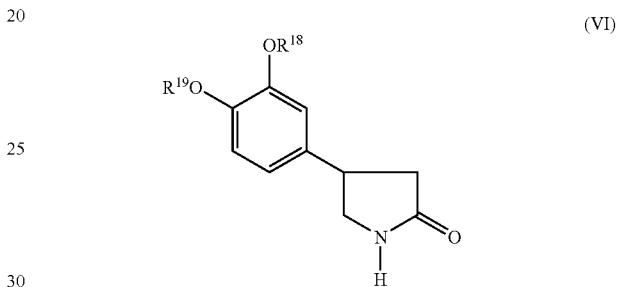

(disclosed and described in U.S. Pat. No. 4,193,926) wherein $R^{18}$ and $R^{19}$ are independently the same or different and are hydrocarbon radicals having up to 18 carbon atoms with at least one being other than methyl, a heterocyclic ring, or alkyl of 1-5 carbon atoms which is substituted by one or more of halogen atoms, hydroxy, carboxy, alkoxy, alkoxycarbonyl or an amino group or amino.

Examples of hydrocarbon $R^{18}$ and $R^{19}$ groups are saturated and unsaturated, straight-chain and branched alkyl of 1-18, preferably 1-5, carbon atoms, cycloalkyl and cycloalkylalkyl, preferably 3-7 carbon atoms, and aryl and aralkyl, preferably of 6-10 carbon atoms, especially monocyclic.

Rolipram is an example of a suitable Type IV phosphodiesterase or PDE inhibitor included within the above formula. Rolipram has the following formula:

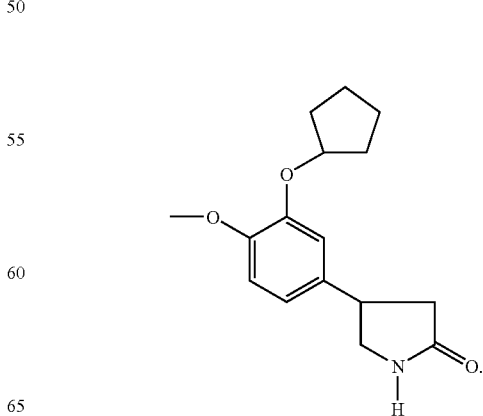

Additional examples of PDE-IV inhibitors are known in the art and include compounds such as, for example, the following:
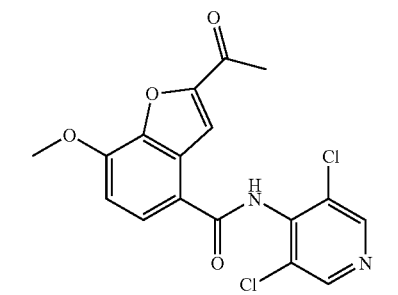
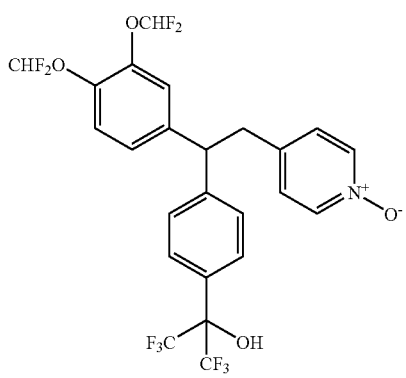
L-791,943
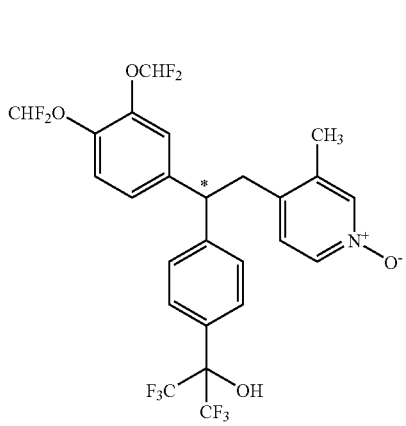
L-826,141
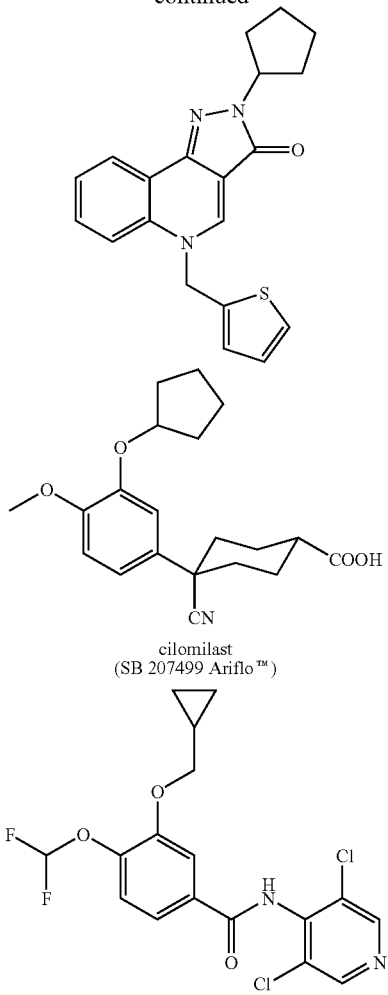
cilomilast
(SB 207499 Ariflo™)
roflumilast
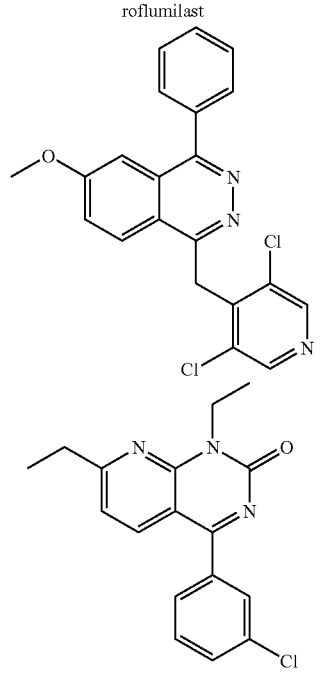
YM976

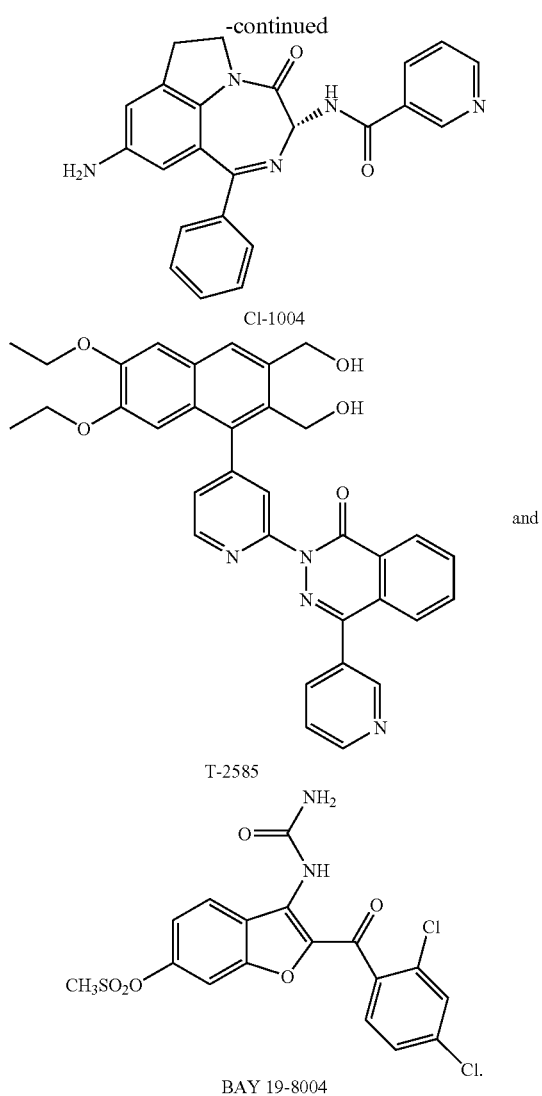

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Compounds of the present invention can conveniently be administered in a pharmaceutical composition containing the compound in combination with a suitable excipient. Such pharmaceutical compositions can be prepared by methods and contain excipients which are well known in the art. A generally recognized compendium of such methods and ingredients is Remington's Pharmaceutical Sciences by E. W. Martin (Mark Publ. Co., 15th Ed., 1975). The compounds and compositions of the present invention can be administered parenterally (for example, by intravenous, intraperitoneal or intramuscular injection), topically, orally, or rectally.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compounds or compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The compound is conveniently administered in unit dosage form; for example, containing about 0.05 mg to about 500 mg, conveniently about 0.1 mg to about 250 mg, most conveniently, about 1 mg to about 150 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The compositions can conveniently be administered orally, sublingually, transdermally, or parenterally at dose levels of about 0.01 to about 150 μg/kg, preferably about 0.1 to about 50 μg/kg, and more preferably about 0.1 to about 10 μg/kg of mammal body weight.

For parenteral administration the compounds are presented in aqueous solution in a concentration of from about 0.1 to about 10%, more preferably about 0.1 to about 7%. The solution may contain other ingredients, such as emulsifiers, antioxidants or buffers.

The exact regimen for administration of the compounds and compositions disclosed herein will necessarily be dependent upon the needs of the individual subject being treated, the type of treatment and, of course, the judgment of the attending practitioner.

The preparation of compounds useful in practicing the present invention are disclosed in and can be prepared using the procedures described in U.S. Pat. No. 6,232,297, U.S. Pat. No. 4,968,697, J. Med. Chem., 1990, 33, 1919-1924, and U.S. patent application Ser. No. 20030186926, filed Oct. 1, 2002, and can generally be prepared as illustrated in Schemes 1A and 1B below. Starting materials can be prepared by procedures described in these schemes, procedures described in the General methods below or by procedures that would be well known to one of ordinary skill in organic chemistry. The variables used in Schemes 1A and Scheme 1B are as defined herein or as in the specification.

The preparation of alkynyl cycloalkanols is illustrated in Scheme 1A. A solution of an appropriate cycloalkanone (where j is from 0-5) is prepared in a solvent such as THF. A solution of a suitable ethynylmagnesium halide compound in a solvent is added to the cycloalkanone. After addition, the solution is allowed to stir at about 20 C for about 20 hours. The reaction is monitored via TLC until the starting material is consumed. The reaction is quenched with water, filtered over a plug of sand and silica, washed with a solvent, such as EtOAc, and evaporated to provide the product. Typically, two products are formed, the isomers formed by the axial/equatorial addition of the alkyne (where m is as defined above, and the sum of m1 and m2 is from 0 to about 7) to the ketone. The compounds are purified via flash chromatography using EtOAc/Hexanes to provide the product.

In accordance with one embodiment of the present invention a composition comprising an agonist of $A_{2A}AR$ is administered to a patient to treat diabetic kidney disease, e.g., diabetic nephropathy. As used herein the term "treating" includes prophylaxis of the specific disorder or condition, or alleviation of the symptoms associated with a specific disorder or condition and/or preventing or eliminating said symptoms. In one embodiment a method for treating diabetic kidney disease, e.g., diabetic nephropathy is provided wherein an agonist of $A_{2A}ARs$ is administered to a patient to reduce inflammation and improve survival in a patient suffering from diabetic kidney disease, e.g., diabetic nephropathy. In one embodiment the $A_{2A}AR$ agonist is selected from the group consisting of ATL146e, ATL-1, ATL-3 and JR-3213.

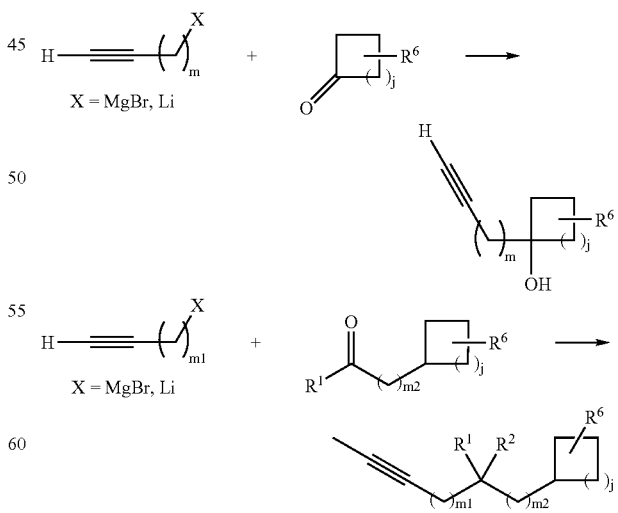

Scheme 1A
General Route to Synthesis of Alkyne Presursors

The preparation of 2-alkynyladenosines is illustrated in Scheme 1B. A flame-dried round bottom under nitrogen is charged with 5-(6-Amino-2-iodo-purin-9-yl)-3,4-dihydroxy-tetrahydro-furan-2-carboxylic acid ethylamide (NECA 2-Iodoadenosine) and a solvent such as DMF. The appropriate alkyne is added followed by acetonitrile and TEA. (The solvents are degassed.) The appropriate alkyne is added in acetonitrile, followed by TEA, 5 mole % Pd(PPh$_3$)$_4$, and CuI. The solution is allowed to stir for about 24 hours at room temperature, and monitored until complete by HPLC. If the reaction is not complete after this time, additional catalyst, CuI, and TEA are added. After the reaction is complete, the solvents are removed under high-vacuum and the residue taken up in a small amount of DMF. This product is isolated using preparative silica TLC. The product is purified by RP-HPLC.

Additional compounds useful in practicing the instant invention are illustrated below:

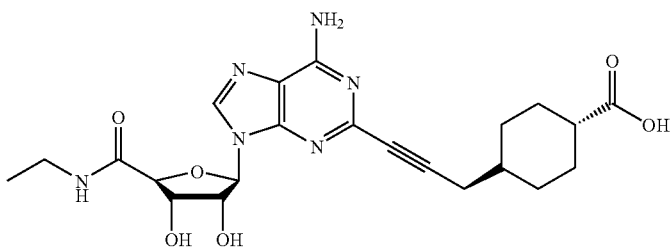

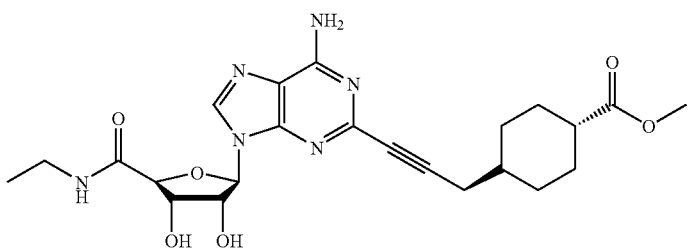

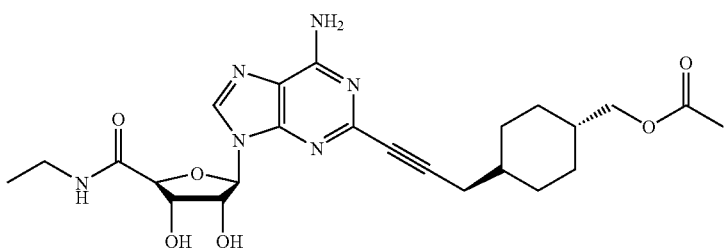

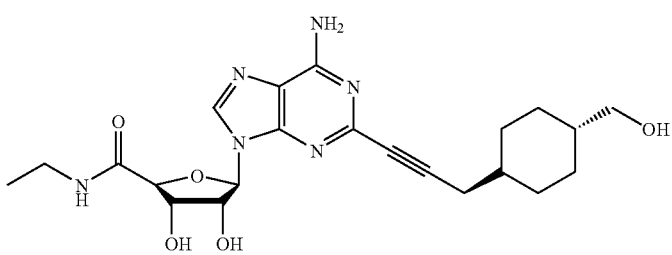

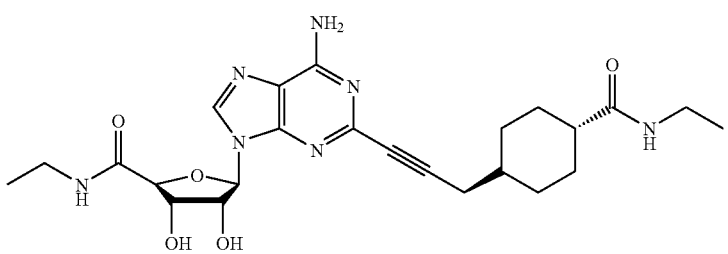

-continued
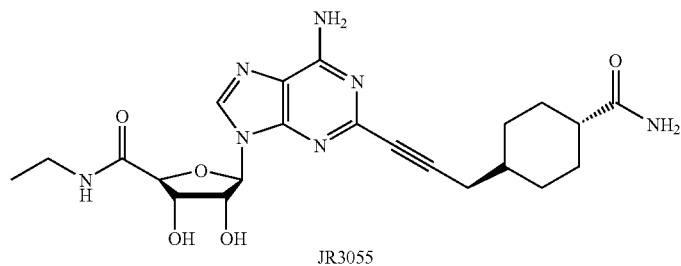
JR3055
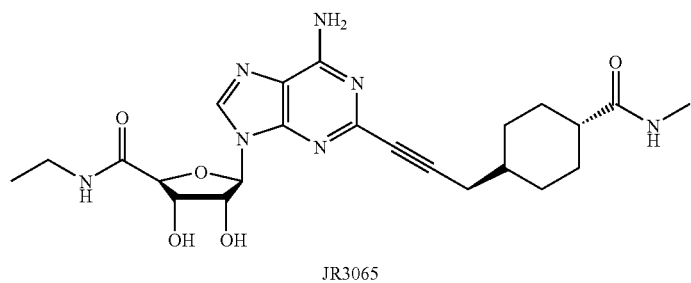
JR3065
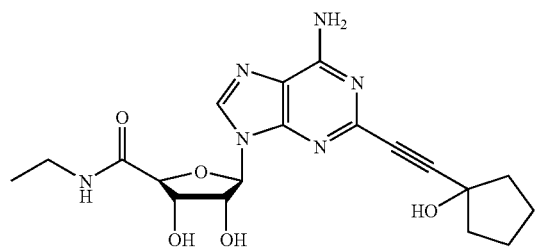
JR3135
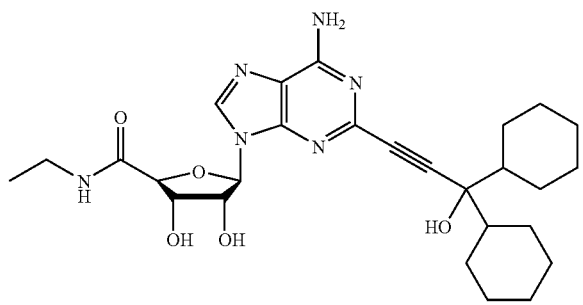
JR3139
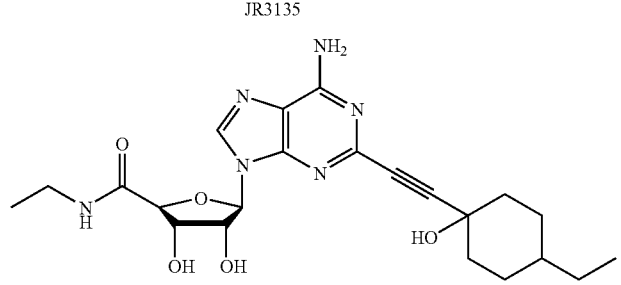
JR3149
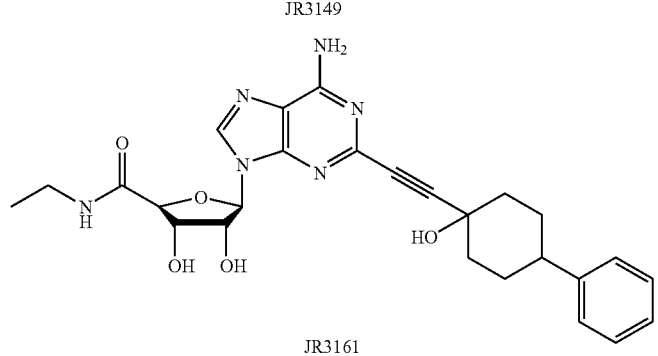
JR3161

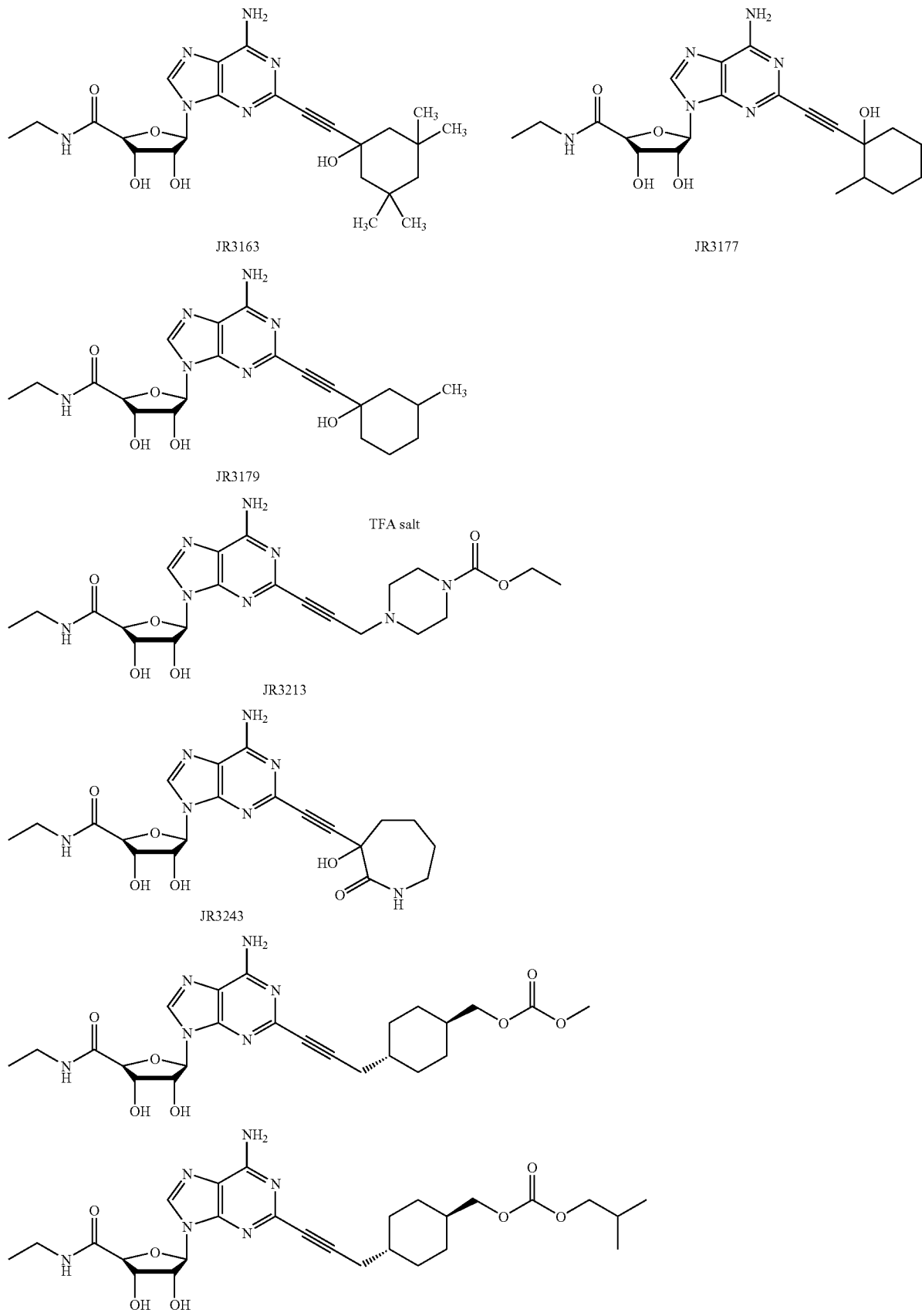
-continued

-continued
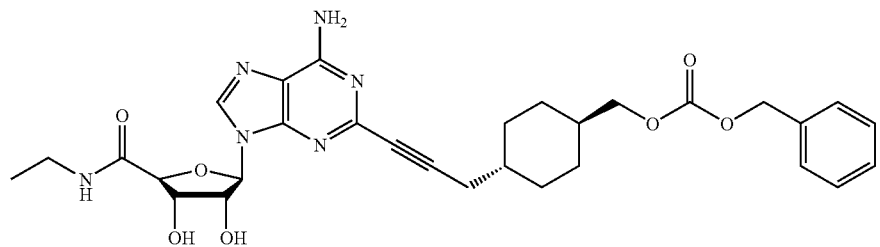
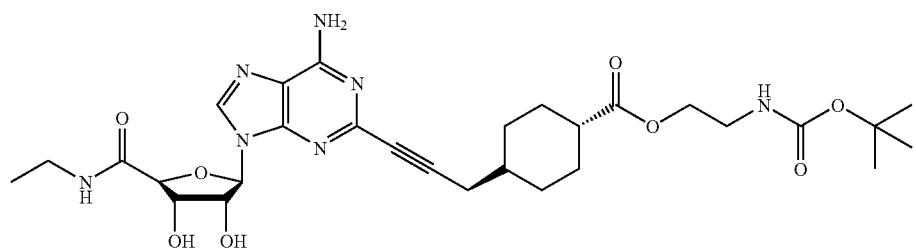
JR3021
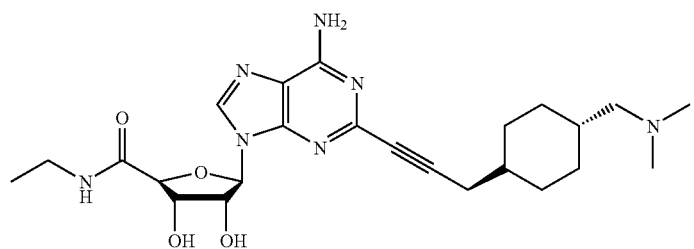
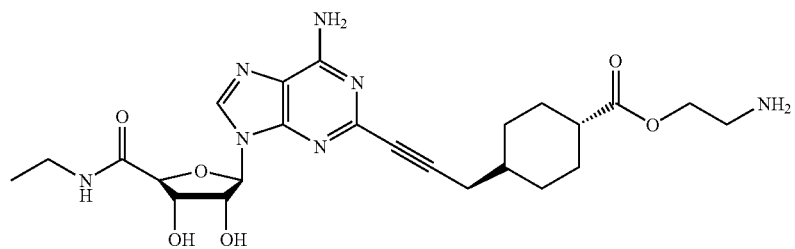
JR3033
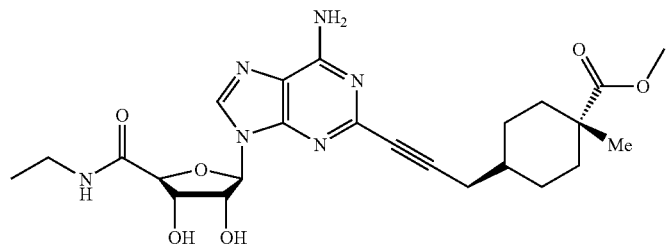
JR3067A
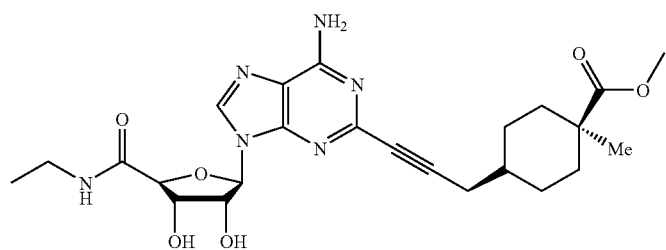
JR3067B -continued
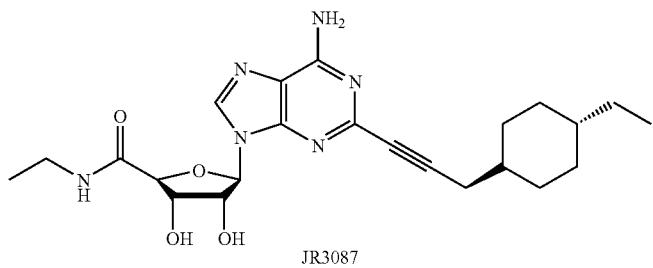
JR3087
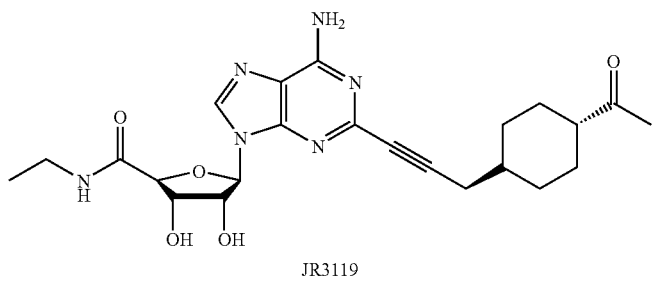
JR3119
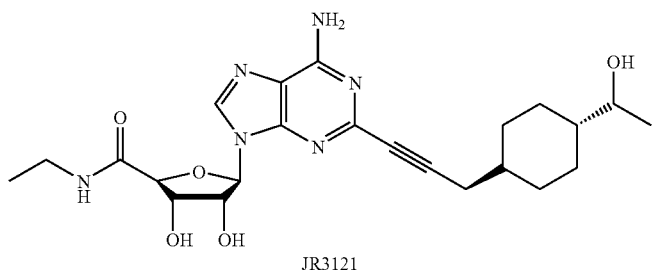
JR3121
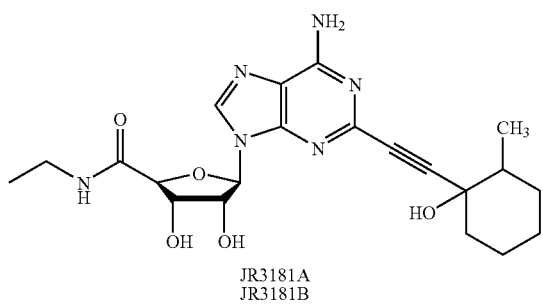
JR3181A
JR3181B
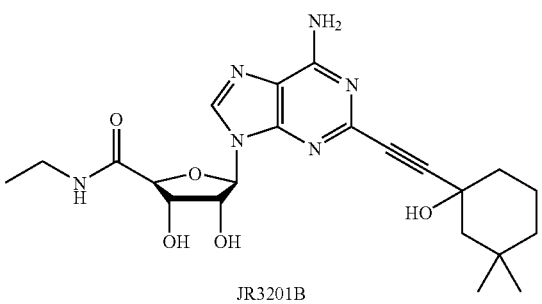
JR3201B
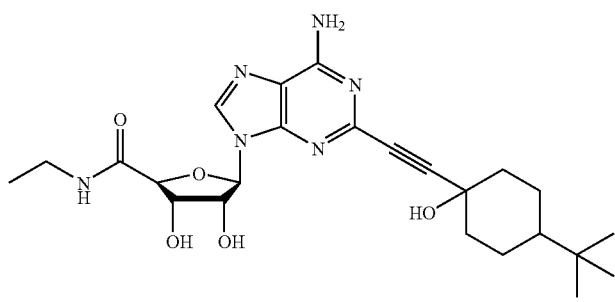
JR3203
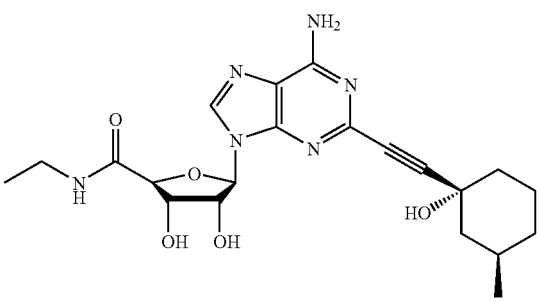
JR3221

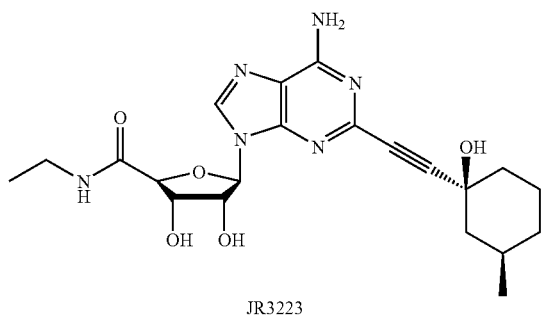
JR3223
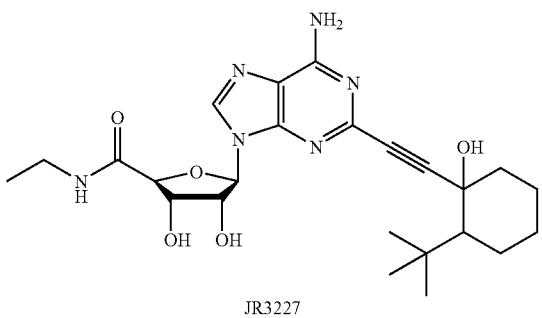
JR3227
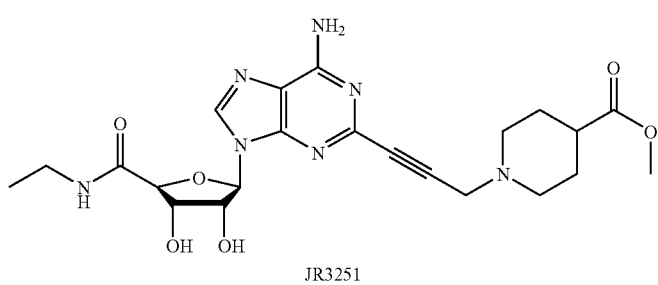
JR3251
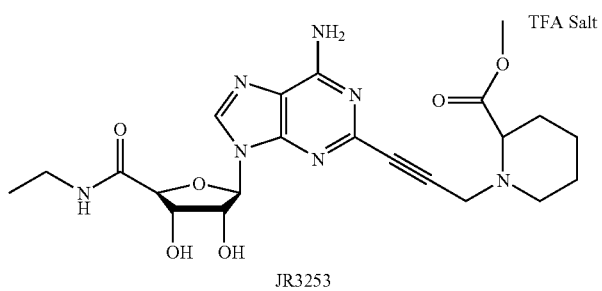
JR3253
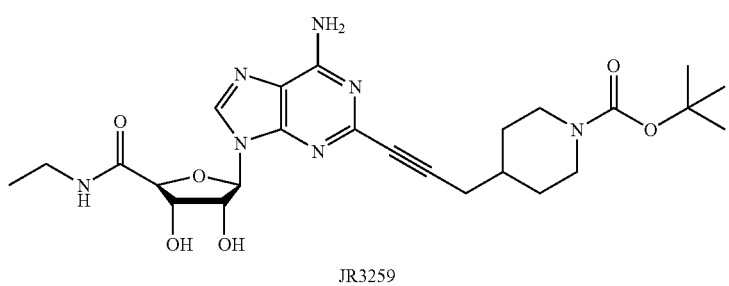
JR3259
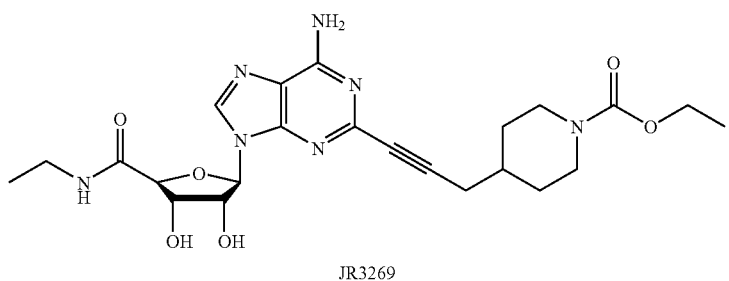
JR3269

-continued
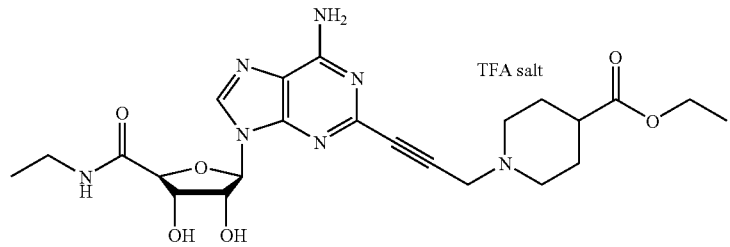
JR3279
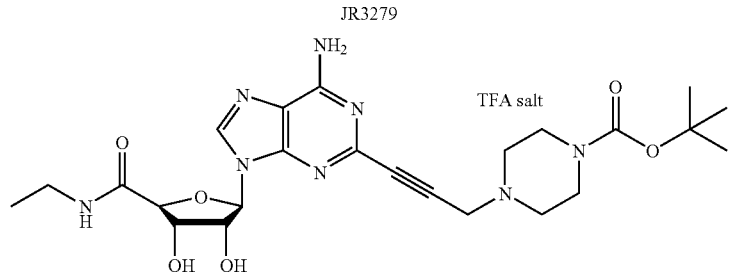
JR3281
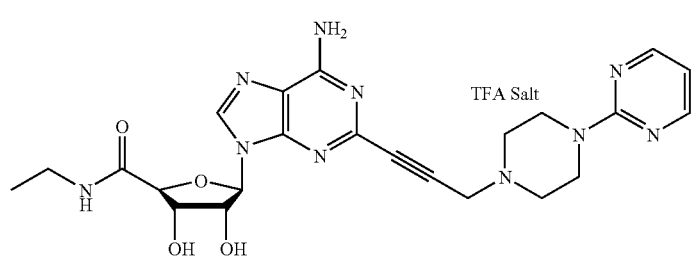
JR3283
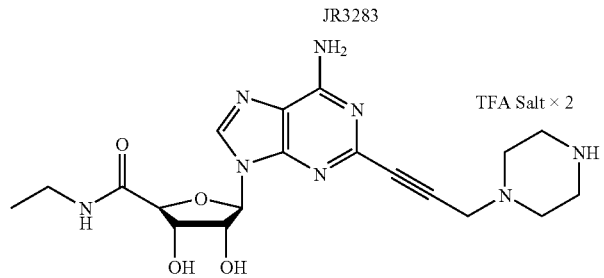
JR3289
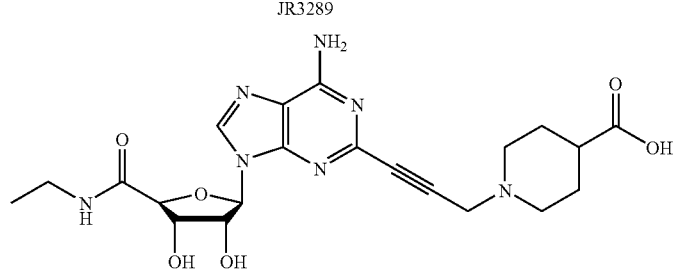
JR3291
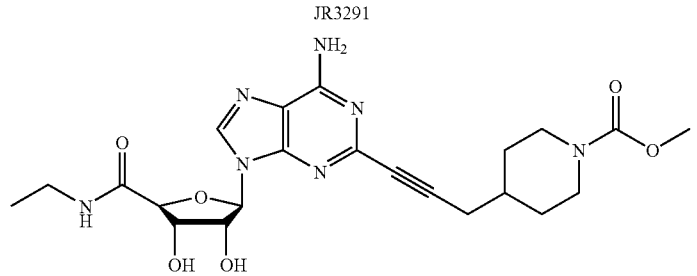
JR4007

-continued
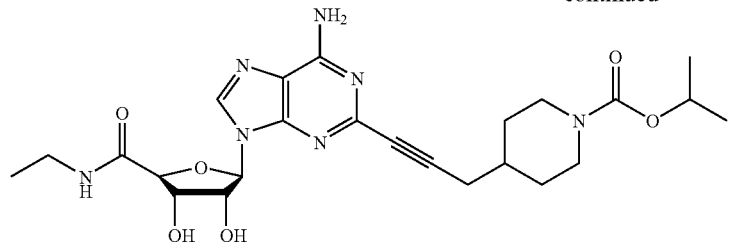
JR4009
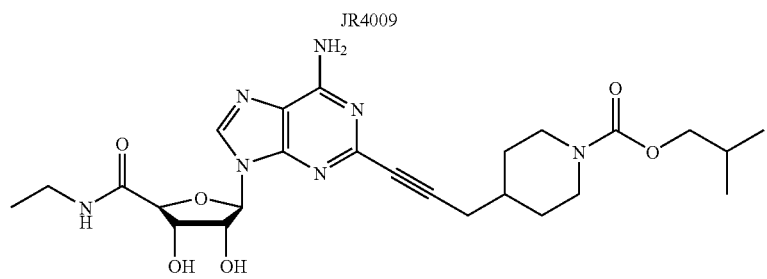
JR4011
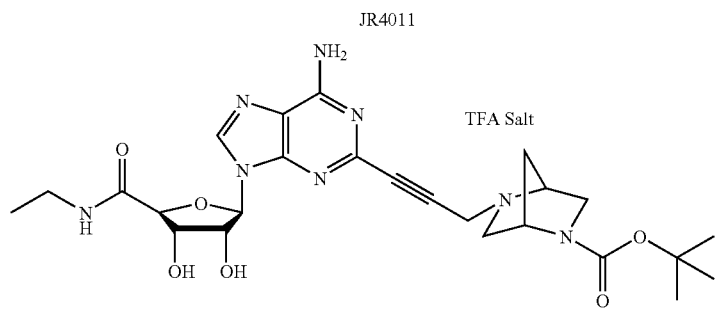
JR4015
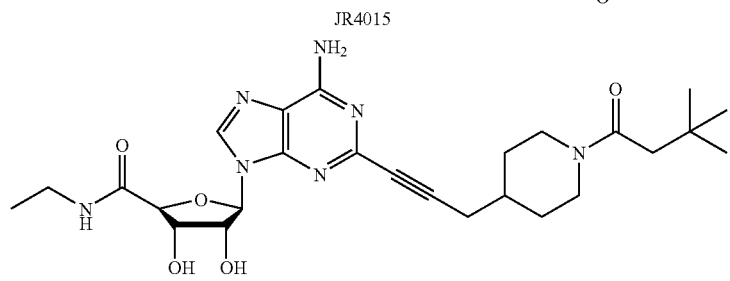
JR4047
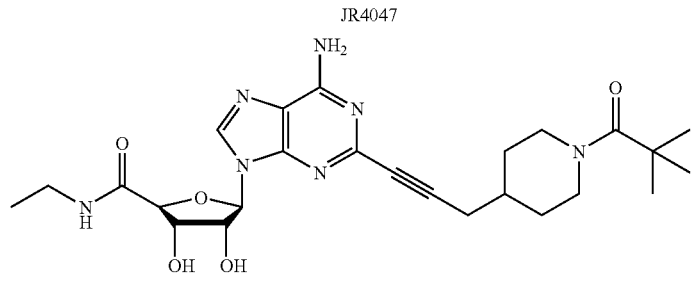
JR4051
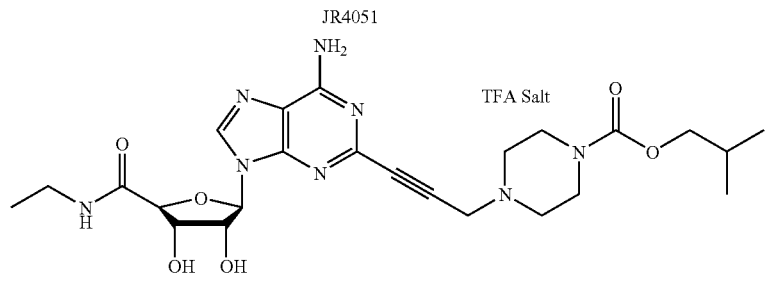
JR4049

-continued
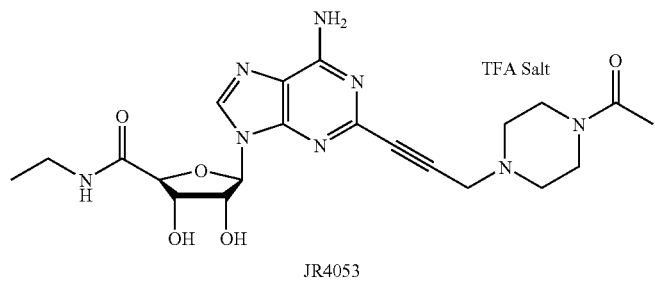
JR4053
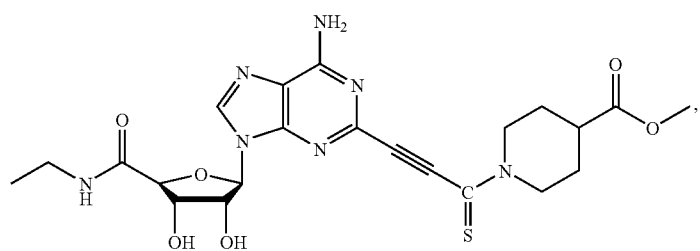
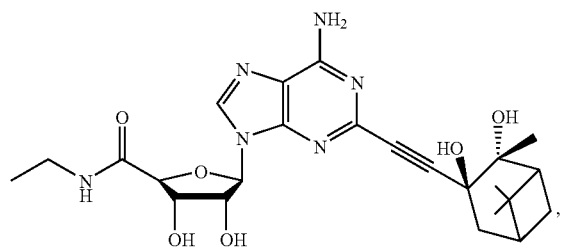
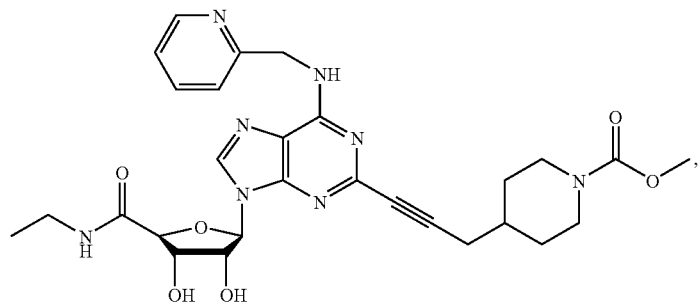
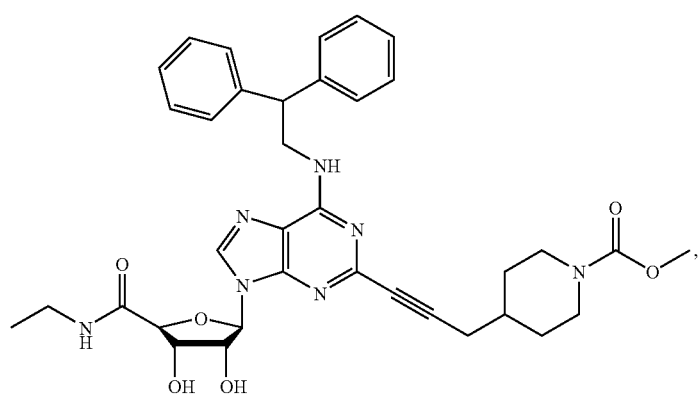

-continued
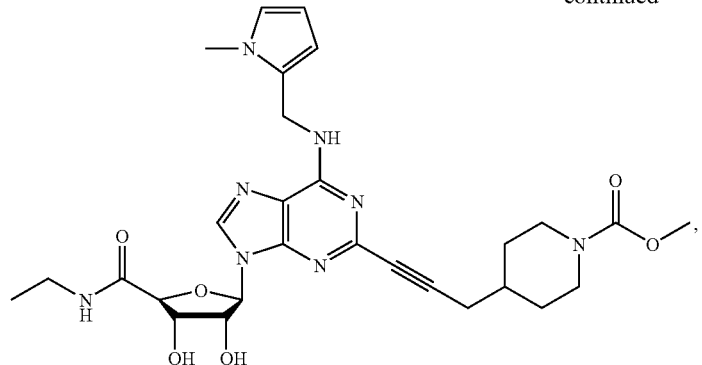
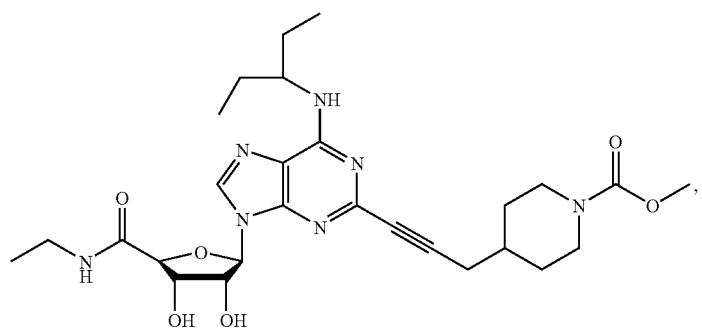
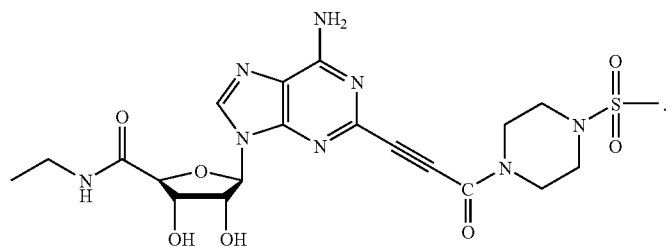
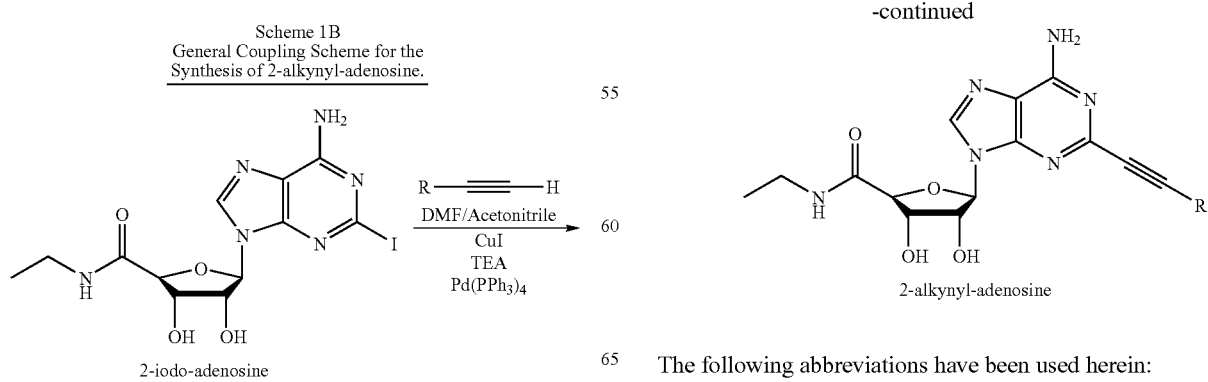
The following abbreviations have been used herein:
2-Aas 2-alkynyladenosines;

125I-ABA N6-(4-amino-3-125iodo-benzyl)adenosine
APCI Atmospheric pressure chemical ionization
ATL146e 4-{3-[6-Amino-9-(5-ethylcarbamoyl-3,4-dihydroxytetrahydro-furan-2-yl)-9H-purin-2-yl]-prop-2-ynyl}cyclo-hexanecarboxylic acid methyl ester;
CCPA 2-chloro-$N^6$-cyclopentyladenosine;
CGS21680 2-[4-(2-carboxyethyl)phenethylamino]-5'-N-ethyl-carboxamidoadenosine;
Cl-IB-MECA N6-3-iodo-2-chlorobenzyladenosine-5'-N-methyl-uronamide;
CPA N6-cyclopentyladenosine
DMF dimethylformamide
DMSO dimethylsulfoxide
DMSO-d6 deuterated dimethylsulfoxide
EtOAc ethyl acetate
eq equivalent
GPCR G protein coupled receptor; $hA_{2A}AR$, Recombinant human $A_{2A}$ adenosine receptor;
IADO 2-Iodoadenosine
$^{125}$I-APE, 2-[2-(4-amino-3-[$^{125}$I]iodophenyl)ethylamino]-adenosine;
NECA 5'-N-ethylcarboxamidoadenosine;
IB-MECA $N^6$-3-iodobenzyladenosine-5'-N-methyluronamide;
2-Iodoadenosine 5-(6-amino-2-iodo-purin-9-yl)-3,4-dihydroxytetra-hydro-furan-2carboxylic acid ethylamide
HPLC high-performance liquid chromatography
HRMS high-resolution mass spectrometry
$^{125}$I-ZM241385, $^{125}$I-4-(2-[7-amino-2-[2-furyl][1,2,4]triazolo-[2,3-a][1,3,5]triazin-5-yl-amino]ethyl)phenol;
INECA 2-iodo-N-ethylcarboxamidoadenosine
LC/MS liquid chromatography/mass spectrometry
m.p. melting point
MHz megahertz
MRS 1220 N-(9-chloro-2-furan-2-yl-[1,2,4]triazolo[1,5-c]-quinazolin-5-yl)-2-phenylacetamide;
MS mass spectrometry
NECA N-ethylcarboxamidoadenosine
NMR nuclear magnetic resonance
RP-HPLC reverse phase high-performance liquid chromatography
TBAF tetrabutylammonium fluoride
TBS tert-butyldimethylsilyl
TBDMSCl tert-butyldimethylsilylchloride
TEA triethylamine
TFA trifluoroacetic acid
THF tetrahydrofuan
TLC thin layer chromatography
p-TSOH para-toluenesulfonic acid
XAC 8-(4-((2-a-minoethyl)aminocarbonyl-methyloxy)-phenyl)-1-3-dipropylxanthine.

Syntheses of Compounds Useful in Practicing the Invention.

All melting points were determined with a Thomas Hoover capillary melting point apparatus and are uncorrected. Nuclear magnetic resonance spectra for proton ($^1$H NMR) were recorded on a 300 MHz GE spectrophotometer. The chemical shift values are expressed in ppm (parts per million) relative to tetramethylsilane. For data reporting, s=singlet, d=doublet, t=triplet, q=quartet, and m=multiplet. Mass spectra were measured on a Finnigan LcQ Classic. High resolution mass spectrometry (HRMS) data was provided by the Nebraska Center for Mass Spectrometry. Analytical HPLC was done on a Waters 2690 Separation Module with a Waters Symmetry C8 (2.1×150 mm) column operated at room temperature. Compounds were eluted at 200 μL/min with 70:30 acetonitrile: water, containing 0.5% acetic acid, with UV detection at 214 nm using a Waters 486 Tunable Detector. Preparative HPLC was performed on a Shimadzu Discovery HPLC with a Shim-pack VP-ODS $C_{18}$ (20×100 mm) column operated at room temperature. Compounds were eluted at 30 mL/min with a gradient 20-80% of water (containing 0.1% TFA) to methanol over 15 minutes with UV detection at 214 nm using a SPD 10A VP Tunable detector. All final compounds presented here were determined to be greater than 98% pure by HPLC. Flash chromatography was performed on Silicyle 60A gel (230-400 mesh) or using reusable chromatography columns and system from RT Scientific, Manchester, N.H. Analytical thin-layer chromatography was done on Merck Kieselgel 60 F254 aluminum sheets. Preparative thin-layer chromatography was done using 1000 micron Analtech Uniplate with silica gel. All reactions were done under a nitrogen atmosphere in flame-dried glassware unless otherwise stated.

EXAMPLE 1

Effects of ATL146e on Blood Glucose, Body Weight, Systolic Blood Pressure and Urine Volume in STZ (45 mg/kg) Diabetic Model (n=5 Each Group)

Rats were administered ATL146e (10 ng/kg/min) or vehicle by osmotic minipumps prior to the induction of diabetes by STZ (50 mg/kg, iv) and followed for up to 6 week. Table 1, below illustrates the effect of STZ on blood glucose, body weight, systolic blood pressure and 24 hours of urine volume as well as the effect of ATL146e.

TABLE 1

| | | Normal | Diabetes | Diabetes + ATL146e |
|---|---|---|---|---|
| Blood Glucose (mg/dl) | Baseline | 71 ± 3 | 74 ± 4 | 75 ± 5 |
| | Week 1 | 67 ± 3 | 366 ± 46** | 311 ± 37** |
| | Week 6 | 73 ± 3 | 375 ± 29*** | 359 ± 23*** |
| Body Weight (g) | Baseline | 250 ± 17 | 250 ± 9 | 250 ± 13 |
| | Week 3 | 391 ± 17** | 344 ± 9* | 323 ± 13* |
| | Week 6 | 505 ± 37*** | 341 ± 22** | 358 ± 24* |
| Systolic Blood Pressure (mmHg) | Week 3 | 120 ± 5 | 117 ± 2 | 123 ± 4 |
| | Week 6 | 115 ± 2 | 145 ± 4***++ | 114 ± 2 |
| 24 h Urine Volume (ml) | Baseline | 27 ± 4 | 18 ± 3 | 15 ± 2 |
| | Week 2 | 18 ± 3 | 72 ± 3*** | 53 ± 13* |
| | Week 4 | 13 ± 3 | 66 ± 6*** | 57 ± 15* |
| | Week 6 | 18 ± 1 | 124 ± 14**+ | 59 ± 23 |

*= 0.05,
**= 0.005,
***= 0.0001 to normal
+= 0.05,
++= 0.0001 to D + ATL146e

Table 1 summarizes the data for blood glucose (BG), body weight (BW), systolic blood pressure (SBP) and 24 hour urinary volume (UV). Basal BG level was 74±4 mg/dl and increased to 325±4 mg/dl 48 hours after STZ-induction of diabetes and continued to be elevated at 3 and 6 weeks of the study period. Normal rats gained weight as expected. The increase in BW in the diabetes and diabetes+ATL146e rats was modest and significant from normal rats of the matched age. There were no significant changes in SBP, 3 weeks after STZ-induction of diabetes between all groups. SBP increased significantly after 6 weeks in the diabetes group from normal animals. Stimulation of $A_{2A}$ receptor with ATL146e restored the increase in SBP that was observed in the diabetes with no treatment. UV increased significantly in diabetes and diabetes+ATL146e groups as expected after STZ-induction of diabetes through out the study period.

EXAMPLE 2

Effects of ATL146e on Urinary Albumin Excretion in Diabetes

Urine collections were obtained for 24 hours for measurement of urinary albumin excretion (UAE). UAE rate was 135±35 μg/24 hours at baseline and increased to 1265±500 μg/24 hours and 2921±335 μg/24 hours (P<0.0001) at week 2 and 6, respectively in the diabetic group. These data confirm that our STZ-induced diabetic animal model demonstrate albuminuria (a marker for diabetic nephropathy). $A_{2A}$ receptor activation with ATL146e minimizes the increase of UAE in diabetic group, a hallmark of diabetic nephropathy. Results are illustrated in FIG. 1.

EXAMPLE 3

Effects of ATL146e on Plasma Creatinine in Diabetes

Figure 2:
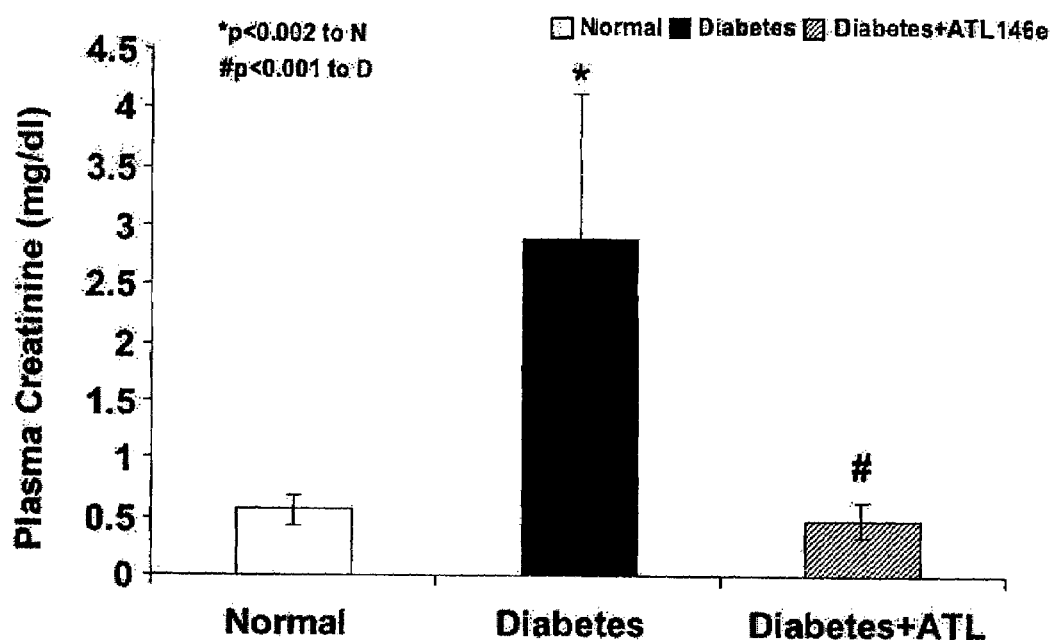

In diabetic rats, ATL146e significantly restored to normal the increase in plasma creatinine that was observed in diabetic mice treated with vehicle. Both reductions in UAE and plasma creatinine levels demonstrate functionally the protective effects of $A_{2A}$ receptor activation in diabetic nephropathy. Results are illustrated in FIG. 2.

EXAMPLE 4

Effects of ATL146e on Urinary and Plasma TNF-Alpha in Diabetes

Figure 3:
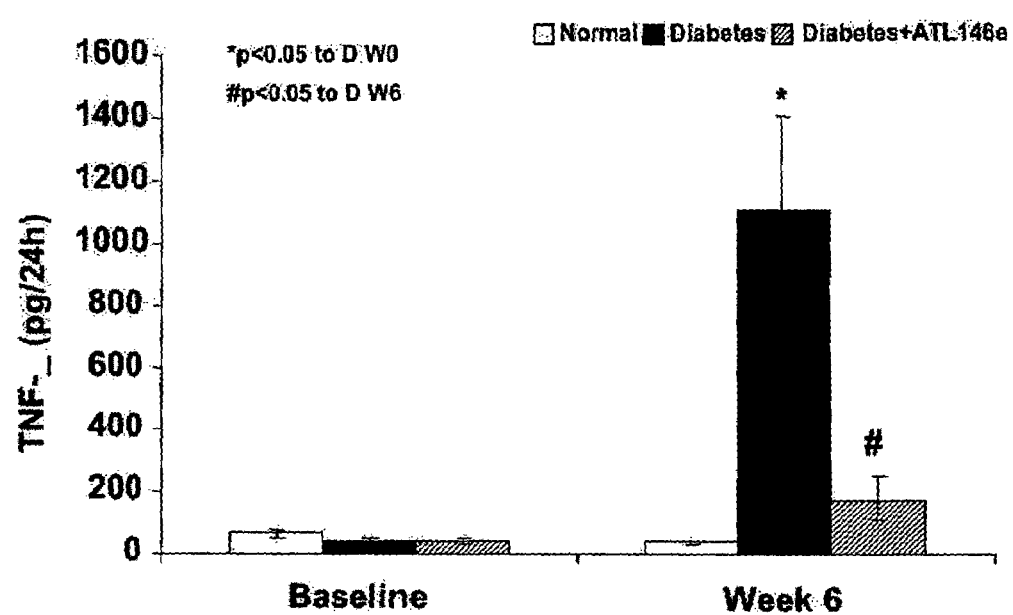

Urinary TNF-alpha was not different between groups before STZ treatment. In the diabetic group, urinary TNF-alpha increased significantly (p<0.05) at 6 week after diabetes. $A_{2A}$ receptor stimulation and ATL146e significantly (P<0.05) reduced the increase in Plasma TNF-alpha. Plasma TNF-alpha was not detectable in all groups at any point of the study periods (data not shown). These data demonstrate that: (1) the increase in inflammatory cytokine TNFalpha in following induction of diabetes is markedly reduced by ATL146e and (2) the source of TNF-alpha is mainly from the kidney as TNF-alpha was not detectable in plasma. Results are illustrated in FIG. 3.

EXAMPLE 5

Figure 4:
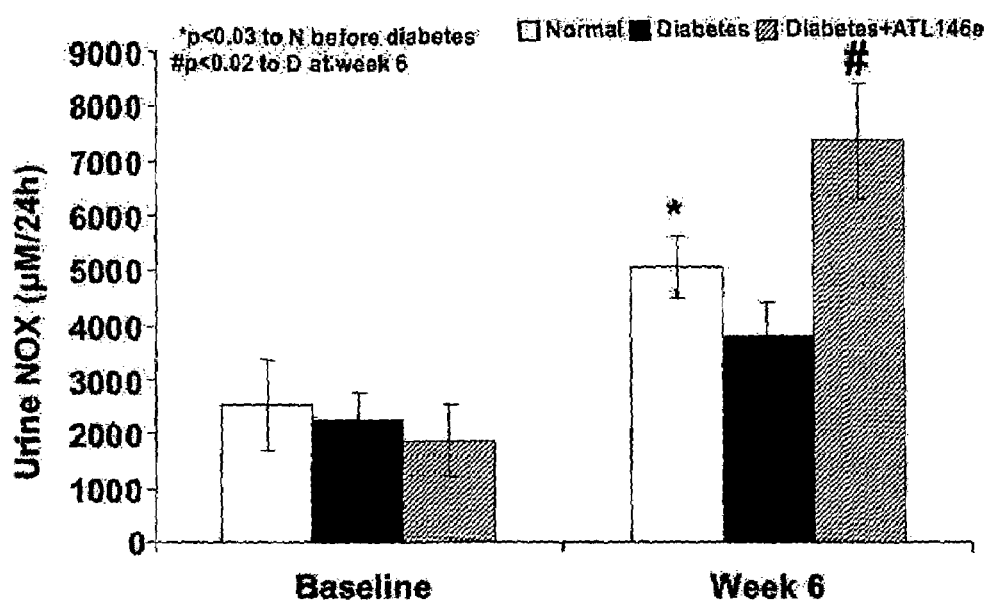

Effects of ATL146e on Urinary Nitric Oxide End Products (Nitrite and Nitrate) (NOX) in Diabetes As shown to the right, NOX (as an indicator of endothelial function in the kidney) was decreased in diabetes group at 6 week after STZ induction of diabetes. The decreased in NOX was improved by ATL146e. The results indicate that the production of NO is diminished in diabetes and restored to normal levels by $A_{2A}$ receptor activation with ATL146e. Results are illustrated in FIG. 4.

EXAMPLE 6

Effects of ATL146e on Fibronectin after Induction of Diabetes

Figure 5:
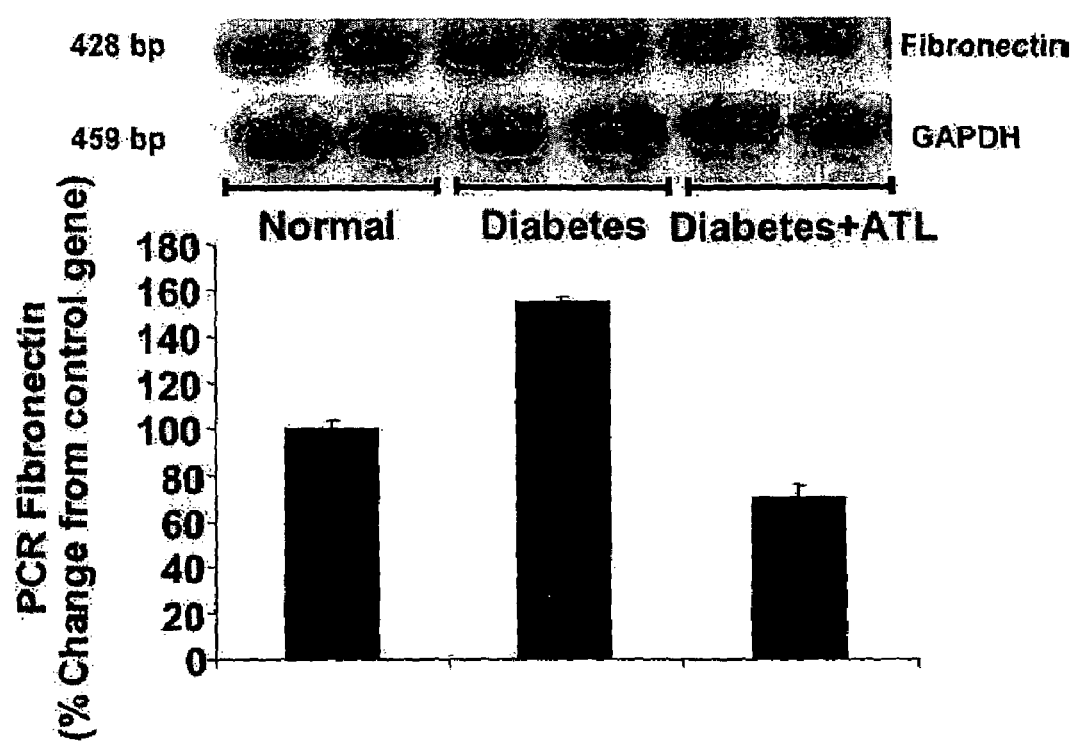

RNA from diabetic rats were extracted and subjected to polymerase chain reaction to examine profibrogenic factors. As shown to the right, the increase in fibronectin mRNA induced by diabetes mellitus was reduced to levels near control in animals following diabetes and treated with ATL146e. FIG. 7 Shows the effect of ATL146e treatment on kidney histology after 6 weeks of diabetes. Trichrome stain of kidneys from diabetic rats treated with vehicle for 6 weeks (Panels a, c) or ATL146e-10 ng/kg/min (Panels b, d). Magnification ×400. Each panel represents a photograph from a different test animal. Results are illustrated in FIG. 5.

EXAMPLE 7

Effect of an $A_{2A}$ AR Agonist (ATL146e) Treatment on Kidney Histology

Figure 6:
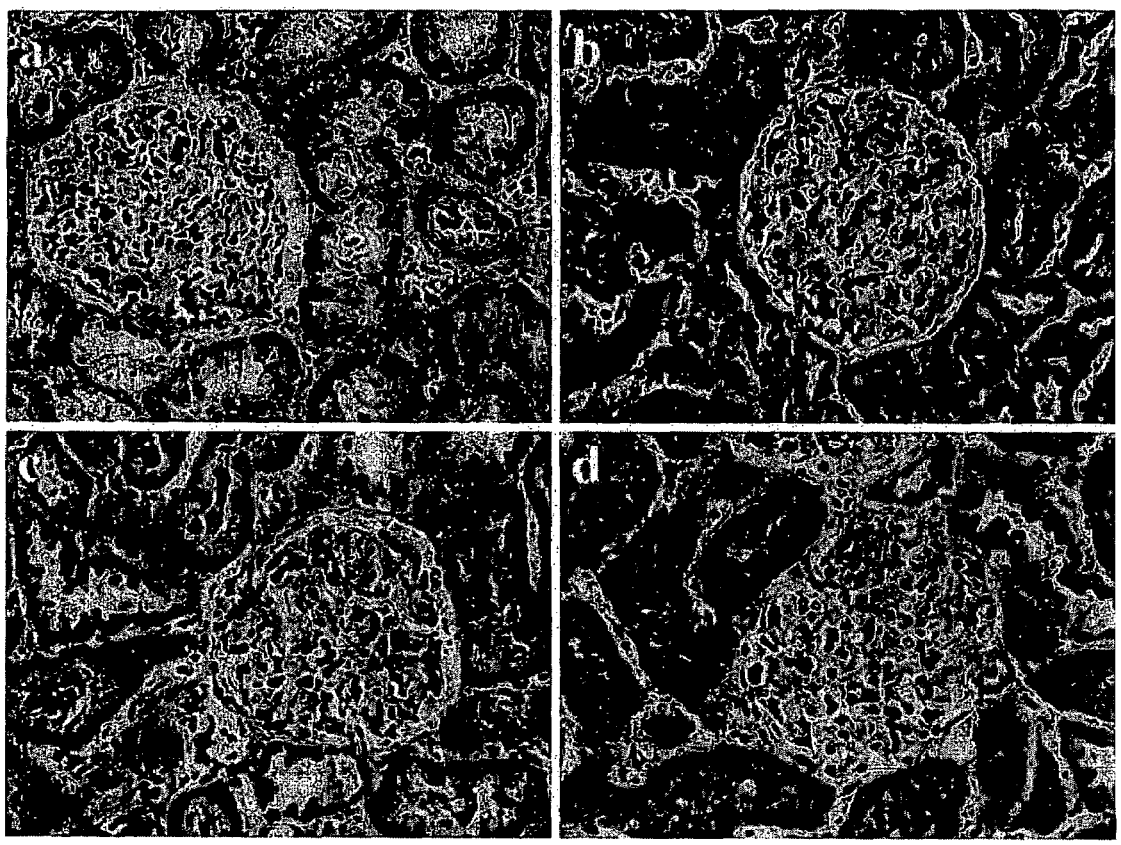
FIG. 6 illustrates the effect of an $A_{2A}$ AR agonist (ATL146e) treatment on kidney histology after 6 weeks of diabetes. Trichrome stain of kidneys from diabetic rats treated with vehicle for 6 weeks (Panels a, and c) or ATL146e-10 ng/kg/min (Panels b, and d). Mag×400. Each panel represents a photograph from separate animals.

Kidneys from diabetic rats were analyzed. A Trichrome stain of kidney samples (Magnification ×400) from the rats treated with vehicle or with ATL146e for 6 weeks is illustrated in FIG. 6. Panels a and c, are samples from rats treated with vehicle alone. Panels b and d, are samples from rats treated with ATL146e (at 10 ng/kg/min). The data illustrate the effect of the $A_{2A}$ AR agonist (ATL146e) treatment on kidney histology after 6 weeks of diabetes. Each panel represents a sample from a different test animal.

All cited publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A therapeutic method for treating diabetic nephropathy comprising the administration to a patient in need thereof an effective amount of an $A_{2A}$ adenosine receptor agonist.

2. The method of claim 1, further comprising administering the $A_{2A}$ adenosine receptor agonist in combination with an effective amount of a Type IV phosphodiesterase inhibitor.

3. The method of claim 1 or 2, wherein the $A_{2A}$ adenosine receptor agonist is a compound having formula (I):

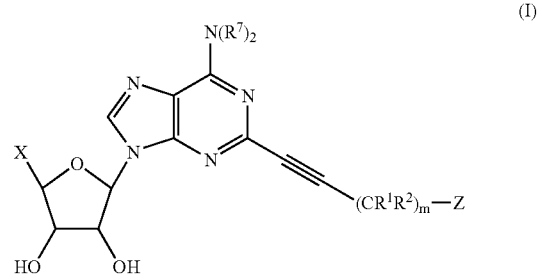

wherein

Z is $CR^3R^4R^5$ or $NR^4R^5$;

each $R^1$ is independently hydrogen, halo, —$OR^a$, —$SR^a$, ($C_1$-$C_8$)alkyl, cyano, nitro, trifluoromethyl, trifluoromethoxy, ($C_3$-$C_8$)cycloalkyl, heterocycle, hetrocycle ($C_1$-$C_8$)alkylene-, aryl, aryl($C_1$-$C_8$)alkylene-, heteroaryl, heteroaryl($C_1$-$C_8$)alkylene-, —$CO_2R^a$, $R^aC(=O)O$—, $R^aC(=O)$—, —$OCO_2R^a$, $R^bR^cNC(=O)O$—, $R^aOC(=O)N(R^b)$—, $R^bR^cN$—, $R^bR^cNC(=O)$—, $R^aC(=O)N(R^b)$—, $R^bR^cNC(=O)N(R^b)$—, $R^bR^cNC(=S)N(R^b)$—, —$OPO_3R^a$, $R^aOC(=S)$—, $R^aC(=S)$—, —$SSR^a$, $R^aS(=O)$—, $R^aS(=O)_2$—, —$N=NR^b$, or —$OPO_2R^a$;

each $R^2$ is independently hydrogen, halo, $(C_1-C_8)$alkyl, $(C_3-C_8)$cycloalkyl, heterocycle, heterocycle$(C_1-C_8)$alkylene-, aryl, aryl$(C_1-C_8)$alkylene-, heteroaryl, or heteroaryl$(C_1-C_8)$alkylene-; or $R^1$ and $R^2$ and the atom to which they are attached is C=O, C=S or C=$NR^d$;

$R^4$ and $R^5$ together with the atoms to which they are attached form a saturated or partially unsaturated, mono-, bicyclic- or aromatic ring having 3, 4, 5, 6, 7, 8, 9 or 10 ring atoms optionally comprising 1, 2, 3, or 4 heteroatoms selected from non-peroxide oxy (—O—), thio (—S—), sulfinyl (—SO—), sulfonyl (—S(O)$_2$—) or amine (—$NR^b$—) in the ring;

wherein any ring comprising $R^4$ and $R^5$ is substituted with from 1 to 14 $R^6$ groups;

wherein each $R^6$ is independently halo, —$OR^a$, —$SR^a$, $(C_1$-$C_8)$alkyl, cyano, nitro, trifluoromethyl, trifluoromethoxy, $(C_1-C_8)$cycloalkyl, $(C_6-C_{12})$bicycloalkyl, heterocycle or hetrocycle $(C_1-C_8)$alkylene-, aryl, aryl $(C_1-C_8)$alkylene-, heteroaryl, heteroaryl$(C_1-C_8)$alkylene-, —$CO_2R^a$, $R^aC(=O)$ O—, $R^aC(=O)$—, —$OCO_2R^a$, $R^bR^cNC(=O)O$—, $R^aOC(=O)N(R^b)$—, $R^bR^cN$—, $R^bR^cNC(=O)$—, $R^aC(=O)N(R^b)$—, $R^bR^cNC(=O)N(R^b)$—, $R^bR^cNC(=S)N(R^b)$—, —$OPO_3R^a$, $R^aOC(=S)$—, $R^aC(=S)$—, —$SSR^a$, $R^aS(=O)$—, —$NNR^b$,—$OPO_2R^a$, or two $R^6$ groups and the atom to which they are attached is C=O, C=S or; two $R^6$ groups together with the atom or atoms to which they are attached can form a carbocyclic or heterocyclic ring;

$R^3$ is hydrogen, halo, —$OR^a$, —$SR^a$, $(C_1-C_8)$alkyl, cyano, nitro, trifluoromethyl, trifluoromethoxy, $(C_3-C_8)$cycloalkyl, heterocycle, hetrocycle$(C_1-C_8)$alkylene-, aryl, aryl$(C_1-C_8)$alkylene-, heteroaryl, heteroaryl$(C_1-C_8)$alkylene-, —$CO_2R^a$, $R^aC(=O)O$—, $R^aC(=O)$—, —$OCO_2R^a$, $R^bR^cNC(=O)O$—, $R^aOC(=O)N(R^b)$—, $R^bR^cN$—, $R^bR^cNC(=O)$—, $R^aC(=O)N(R^b)$—, $R^bR^cNC(=O)N(R^b)$—, $R^bR^cNC(=S)N(R^b)$—, —$OPO_3R^a$, $R^aOC(=S)$—, $R^aC(=S)$—, —$SSR^a$, $R^aS(=O)$—, $R^aS(=O)_2$—, —$NNR^b$, —$OPO_2R^a$; or if the ring formed from $CR^4R^5$ is aryl or hetreroaryl or partially unsaturated then $R^3$ can be absent;

each $R^7$ is independently hydrogen, $(C_1-C_8)$alkyl, $(C_3-C_8)$cycloalkyl, aryl or aryl$(C_1-C_8)$alkylene, heteroaryl, heteroaryl$(C_1-C_8)$alkylene-;

X is —$CH_2OR^a$, —$CO_2R^a$, —$OC(O)R^a$, —$CH_2OC(O)R^a$, —$C(O)NR^bR^c$, —$CH_2SR^a$, —$C(S)OR^a$, —$OC(S)R^a$, —$CH_2OC(S)R^a$ or —$C(S)NR^bR^c$ or —$CH_2N(R^b)(R^c)$;

wherein any of the alkyl, cycloalkyl, heterocycle, aryl, or heteroaryl, groups of $R^1$, $R^2$, $R^3$, $R^6$ and $R^7$ is optionally substituted on carbon with one or more (e.g. 1, 2, 3, or 4) substituents selected from the group consisting of halo, —$OR^a$, —$SR^a$, $(C_1-C_8)$alkyl, cyano, nitro, trifluoromethyl, trifluoromethoxy, $(C_3-C_8)$cycloalkyl, $(C_6-C_{12})$bicycloalkyl, heterocycle or hetrocycle$(C_1-C_8)$alkylene-, aryl, aryloxy, aryl $(C_1-C_8)$alkylene-, heteroaryl, heteroaryl$(C_1-C_8)$alkylene-, —$CO_2R^a$, $R^aC(=O)O$—, $R^aC(=O)$—, —$OCO_2R^a$, $R^bR^cNC(=O)O$—, $R^aOC(=O)N(R^b)$—, $R^bR^cN$—, $R^bR^cNC(=O)$—, $R^aC(=O)N(R^b)$—, $R^bR^cNC(=O)N(R^b)$—, $R^bR^cNC(=S)N(R^b)$—, $OPO_3R^a$, $R^aOC(=S)$—, $R^aC(=S)$, —$SSR^a$, $R^aS(=O)_p$—, $R^bR^cNS(O)_p$—, N=$NR^b$, and —$OPO_2R^a$;

wherein any $(C_1-C_8)$alkyl, $(C_3-C_8)$cycloalkyl, $(C_6-C_{12})$bicycloalkyl, $(C_1-C_8)$alkoxy, $(C_1-C8)$alkanoyl, $(C_1-C_8)$alkylene, or heterocycle, is optionally partially unsaturated;

each $R^a$, $R^b$ and $R^c$ is independently hydrogen, $(C_1-C_8)$alkyl, or $(C_1-C_8)$alkyl substituted with 1-3 $(C_1-C_8)$ alkoxy, $(C_3-C_8)$cycloalkyl, $(C_1-C_8)$alkylthio, amino acid, aryl, aryl$(C_1-C_8)$alkylene, heteroaryl, or heteroaryl $(C_1-C_8)$alkylene; or $R^b$ and $R^c$, together with the nitrogen to which they are attached, form a pyrrolidino, piperidino, morpholino, or thiomorpholino ring; and $R^d$ is hydrogen or $(C_1-C_6)$alkyl;

m is 0 to about 8 and p is 0 to 2;

or a pharmaceutically acceptable salt thereof.

4. The method of claim 3, wherein $R^1$ is hydrogen, —OH, —$CH_2OH$, —OMe, —OAc, —$NH_2$, —NHMe, —$NMe_2$ or —NHAc.

5. The method of any of claim 4, wherein $R^1$ is hydrogen, —OH, —OMe, —OAc, —$NH_2$, —NHMe, —$NMe_2$ or —NHAc.

6. The method of claim 5, wherein $R^1$ is hydrogen, OH, OMe, or $NH_2$.

7. The method of claim 6, wherein $R^1$ is hydrogen, OH, or $NH_2$.

8. The method of claim 7, wherein $R^1$ is hydrogen or OH.

9. The method of claim 8, wherein $R^2$ is hydrogen, $(C_1-C_8)$ alkyl, cyclopropyl, cyclohexyl or benzyl.

10. The method of claim 9, wherein $R^2$ is hydrogen, methyl, ethyl or propyl.

11. The method of claim 10, wherein $R^2$ is hydrogen or methyl.

12. The method of claim 11, wherein $R^2$ is hydrogen.

13. The method of claim 8, wherein $R^1$, $R^2$ and the carbon atom to which they are attached is carbonyl (C=O).

14. The method of claim 13, wherein $R^3$ is hydrogen, OH, OMe, OAc, $NH_2$, NHMe, $NMe_2$ or NHAc.

15. The method of claim 14, wherein $R^3$ is hydrogen, OH, OMe, or $NH_2$.

16. The method of claim 15, wherein $R^3$ is hydrogen, OH, or $NH_2$.

17. The method of claim 16, wherein $R^3$ is hydrogen or OH.

18. The method of claim 3, wherein the ring comprising $R^4$, $R^5$ and the atom to which they are connected is cyclopentane, cyclohexane, piperidine, dihydro-pyridine, tetrahydro-pyridine, pyridine, piperazine, decaline, tetrahydro-pyrazine, dihydro-pyrazine, pyrazine, dihydro-pyrimidine, tetrahydro-pyrimidine, hexahydro-pyrimidine, pyrazine, imidazole, dihydro-imidazole, imidazolidine, pyrazole, dihydro-pyrazole, and pyrazolidine.

19. The method of claim 18, wherein the ring comprising $R^4$, $R^5$ and the atom to which they are connected is cyclopentane, cyclohexane, piperidine, dihydro-pyridine, tetrahydro-pyridine, pyridine, piperazine, tetrahydro-pyrazine, dihydro-pyrazine, pyrazine, dihydro-pyrimidine, tetrahydro-pyrimidine, hexahydro-pyrimidine, pyrazine, imidazole, dihydro-imidazole, imidazolidine, pyrazole, dihydro-pyrazole, and pyrazolidine.

20. The method of claim 19, wherein the ring comprising $R^4$ and $R^5$ and the atom to which they are connected is, cyclohexane, piperidine or piperazine.

21. The method of claim 3, wherein $R^6$ is $(C_1-C_8)$alkyl, or substituted $(C_1-C_8)$alkyl, —$OR^a$, —$CO_2R^a$, $R^aC(=O)$—, $R^aC(=O)O$—, $R^bR^cN$—, $R^bR^cNC(=O)$—, or aryl.

22. The method of claim 21, wherein $R^6$ is $(C_1-C_8)$alkyl, —$OR^a$, —$CO_2R^a$, $R^aC(=O)$—, $RaC(=O)O$—, $R^bR^cN$—, $R^bR^cNC(=O)$—, or aryl.

23. The method of claim 22, wherein $R^6$ is methyl, ethyl, butyl, OH, $OR^a$, —$CO_2R^a$, $R^aC(=O)$—, $OC(=O)CH_2CH_3$, —$CONR^bR^c$, $NR^bR^c$ or phenyl.

24. The method of claim 23, wherein $R^6$ is OH, OMe, methyl, ethyl, t-butyl, —$CO_2R^a$, —$CONR^bR^c$, OAc, $NH_2$, NHMe, $NMe_2$, NHEt or $N(Et)_2$.

25. The method of claim 24, wherein $R^6$ is methyl, ethyl, t-butyl, phenyl, $-CO_2R^a$ $-CONR^bR^c$, or $(=O)CR^a$.

26. The method of claim 25, wherein $R^6$ is methyl, ethyl, $-CO_2R^a$—$CONR^bR^c$, or OAc.

27. The method of claim 26, wherein $R^6$ is $-(CH_2)_{1-2}OR^a$, $-(CH_2)_{1-2}C(=O)OR^a$, $-(CH_2)_{1-2}OC(=O)R^a$, $-(CH_2)_{1-2}C(=O)R^a$, $-(CH_2)_{1-2}OCO_2R^a$, $-(CH_2)_{1-2}NHR^4$, $-(CH_2)_{1-2}NR^bR^c$, $-(CH_2)_{1-2}OC(=O)NHR^a$, or $-(CH_2)_{1-2}OC(=O)NR^bR^c$.

28. The method of claim 27, wherein $R^6$ is $-CH_2OH$, $-CH_2OAc$, $-CH_2OCH_3$, $-CH_2C(=O)OCH_3$, $-CH_2OC(=O)CH_3$, $-CH_2C(=O)CH_3$, $-CH_2OCO_2CH_3$, $-CH_2NH(CH_3)$, or $-(CH_2)_{1-2}N(CH_3)_2$.

29. The method of claim 28, wherein $R^6$ is $-CH_2OH$, $-CH_2OAc$, $-C(=O)OCH_3$, $-C(=O)CH_3$, $OCO_2CH_3$—$OCO_2CH_3$, $-CH_2NH(CH_3)$, or $-(CH_2)_{1-2}N(CH_3)_2$.

30. The method of claim 3, wherein number of $R^6$ groups substituted on the $R^4R^5$ ring is from 1 to about 4.

31. The method of claim 30, wherein $R^a$ and $R^b$ are independently hydrogen, $(C_1-C_4)$alkyl, aryl or aryl$(C_1-C_8)$alkylene.

32. The method of claim 31, wherein $R^a$ and $R^b$ are independently hydrogen, methyl or ethyl, phenyl or benzyl.

33. The method of claim 32, wherein $R^a$ is $(C_1-C_8)$alkyl.

34. The method of claim 33, wherein $R^a$ is methyl, ethyl, propyl or butyl.

35. The method of claim 34, wherein $R^a$ is, methyl, ethyl, i-propyl, i-butyl or tert-butyl.

36. The method of claim 3, wherein $R^b$ and $R^c$ and the atom to which they are attached form a ring.

37. The method of claim 3, wherein $R^7$ is hydrogen, alkyl, aryl or aryl$(C_1-C_8)$alkylene.

38. The method of claim 37, wherein $R^7$ is hydrogen, methyl or ethyl, phenyl or benzyl.

39. The method of claim 38, wherein $R^7$ is H, or methyl.

40. The method of claim 38, wherein $N(R^7)_2$ is amino, methylamino, dimethylamino; ethylamino; pentylamino, diphenylethylamino, pyridylmethylamino, diethylamino or benzylamino.

41. The method of claim 40, wherein $-N(R^7)_2$ is amino, methylamino, dimethylamino; ethylamino; diethylamino or benzylamino.

42. The method of claim 41, wherein $N(R^7)_2$ is amino, or methylamino.

43. The method of claim 3, wherein X is $-CH_2OR^a$, $-CO_2R^a$, $-OC(O)R^a$, $-CH_2OC(O)R^a$, $-C(O)NR^bR^c$.

44. The method of claim 43, wherein X is $-CH_2OR^a$ or $-C(O)NR^bR^c$.

45. The method of claim 44, wherein X is $-CH_2OH$ or $-C(O)NHCH_2CH_3$.

46. The method of claim 3, wherein m is 0, 1, or 2.

47. The method of claim 3 wherein the rings comprising $R^4$, $R^5$ and the atom to which they are connected are selected from the group consisting of:

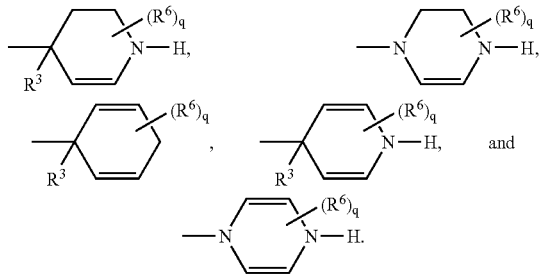

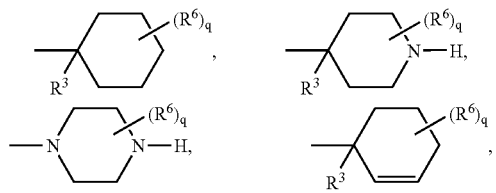

48. The method of claim 47, wherein the rings comprising $R^4$, $R^5$ and the atom to which they are connected are selected from the group consisting of:

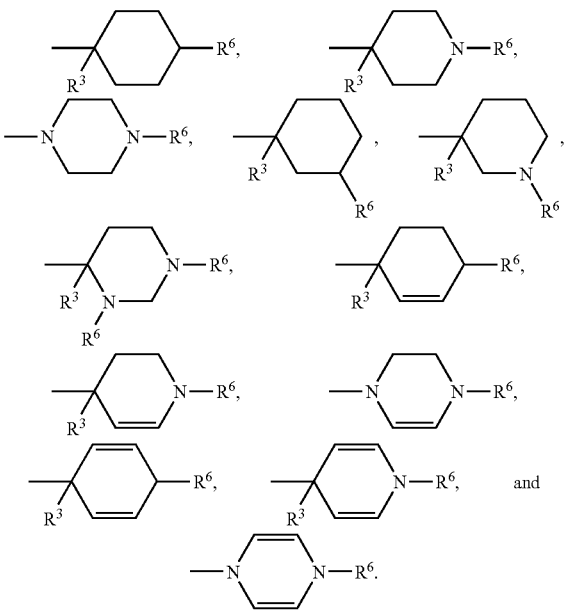

49. The method of claim 47, wherein the ring comprising $R^4$ and $R^5$ is 2-methylcyclohexane, 2,2-dimethylcyclohexane, 2-phenylcyclohexane, 2-ethylcyclohexane, 2,2-diethylcyclohexane, 2-tert-butylcyclohexane, 3-methylcyclohexane, 3,3-dimethylcyclohexane, 4-methylcyclohexane, 4-ethylcyclohexane, 4-phenyl cyclohexane, 4-tert-butylcyclohexane, 4-carboxymethyl cyclohexane, 4-carboxyethyl cyclohexane, 3,3,5,5-tetramethyl cyclohexane, 2,4-dimethyl cyclopentane, 4-cyclohexanecarboxyic acid, 4-cyclohexanecarboxyic acid esters, or 4-methyloxyalkanoyl-cyclohexane.

50. The method of claim 47, wherein the ring comprising $R^4$ and $R^5$ is 4-piperidine, 4-piperidene-1-carboxylic acid, 4-piperidine-1-carboxylic acid methyl ester, 4-piperidine-1-carboxylic acid ethyl ester, 4-piperidine-1-carboxylic acid propyl ester, 4-piperidine-1-carboxylic acid tert-butyl ester, 1-piperidine, 1-piperidine-4-carboxylic acid methyl ester, 1-piperidine-4-carboxylic acid ethyl ester, 1-piperidine-4-carboxylic acid propyl ester, 1-piperidine-4-caboxylic acid tert-butyl ester, 1-piperidine-4-carboxylic acid methyl ester, 3-piperidine, 3-piperidene-1-carboxylic acid, 3-piperidine-1-carboxylic acid methyl ester, 3-piperidine-1-carboxylic acid tert-butyl ester, 1,4-piperazine, 4-piperazine-1-carboxylic acid, 4-piperazine-1-carboxylic acid methyl ester, 4-piperazine-1-carboxylic acid ethyl ester, 4-piperazine-1-carboxylic acid acid propyl ester, 4-piperazine-1-carboxylic acid tert-butylester, 1,3-piperazine, 3-piperazine-1-carboxylic acid, 3-piperazine-1-carboxylic acid methyl ester, 3-piperazine-1-carboxylic acid ethyl ester, 3-piperazine-1-carboxylic acid propyl ester, 3-piperidine-1-carboxylic acid tert-butylester, 1-piperidine-3-carboxylic acid methyl ester, 1-piperidine-3-carboxylic acid ethyl ester, 1-piperidine-3-carboxylic acid propyl ester or 1-piperidine-3-caboxylic acid tert-butyl ester.

51. The method of claim 50, wherein the ring comprising R⁴ and R⁵ is 2-methyl cyclohexane, 2,2-dimethylcyclohexane, 2-phenyl cyclohexane, 2-ethylcyclohexane, 2,2-diethylcyclohexane, 2-tert-butyl cyclohexane, 3-methyl cyclohexane, 3,3-dimethylcyclohexane, 4-methyl cyclohexane, 4-ethylcyclohexane, 4-phenyl cyclohexane, 4-tert-butyl cyclohexane, 4-carboxymethyl cyclohexane, 4-carboxyethyl cyclohexane, 3,3,5,5-tetramethyl cyclohexane, 2,4-dimethyl cyclopentane, 4-piperidine-1-carboxylic acid methyl ester, 4-piperidine-1-carboxylic acid tert-butyl ester 4-piperidine, 4-piperazine-1-carboxylic acid methyl ester, 4-piperidine-1-carboxylic acid tert-butylester, 1-piperidine-4-carboxylic acid methyl ester, 1-piperidine-4-caboxylic acid tert-butyl ester, tert-butylester, 1-piperidine-4-carboxylic acid methyl ester, or 1-piperidine-4-caboxylic acid tert-butyl ester, 3-piperidine-1-carboxylic acid methyl ester, 3-piperidine-1-carboxylic acid tert-butyl ester, 3-piperidine, 3-piperazine-1-carboxylic acid methyl ester, 3-piperidine-1-carboxylic acid tert-butylester, 1-piperidine-3-carboxylic acid methyl ester, 1-piperidine-3-caboxylic acid tert-butyl ester.

52. The method of claim 3, wherein the A$_{2A}$ adenosine receptor compound has the formula:

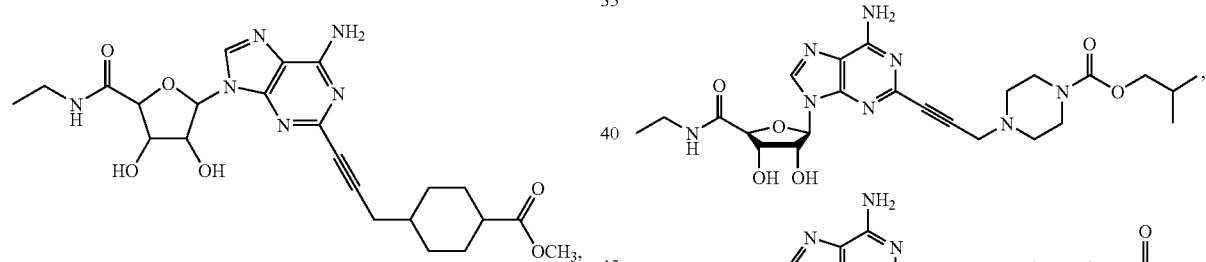

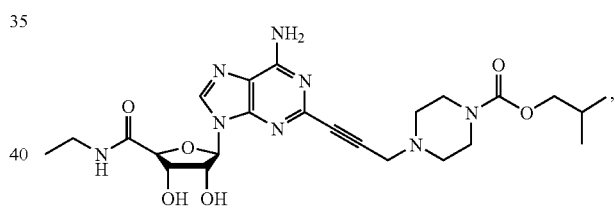

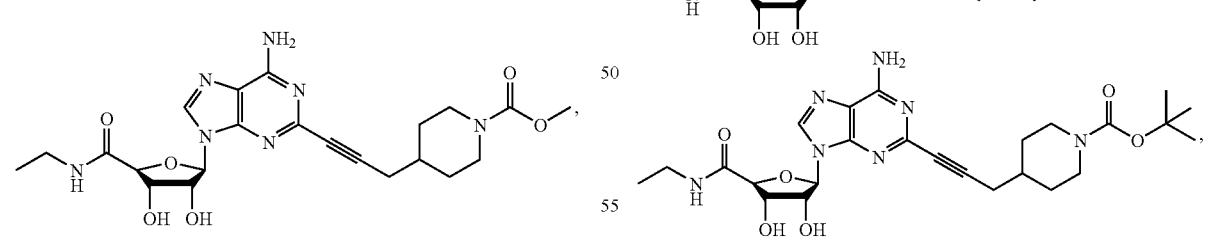

-continued

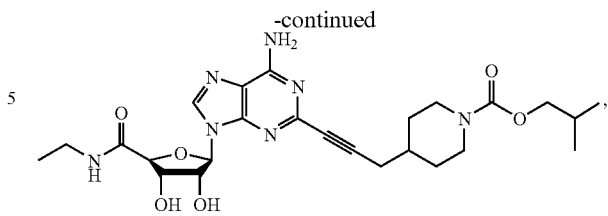

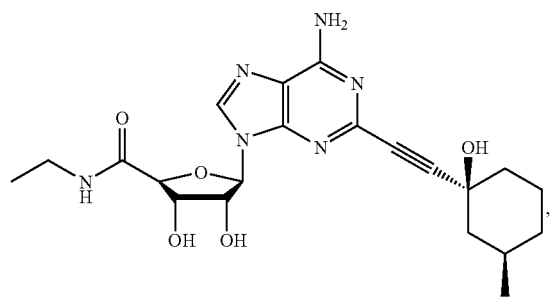

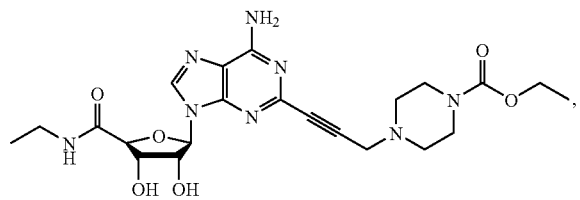

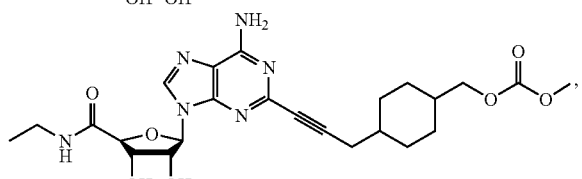

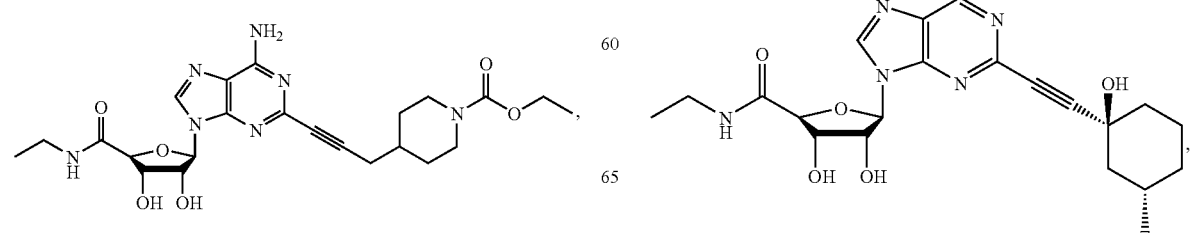

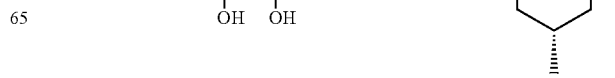

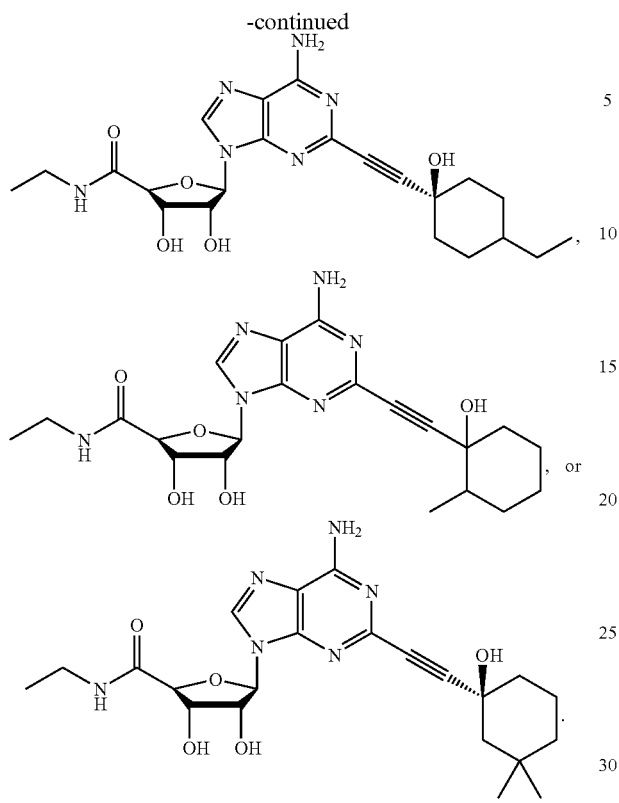

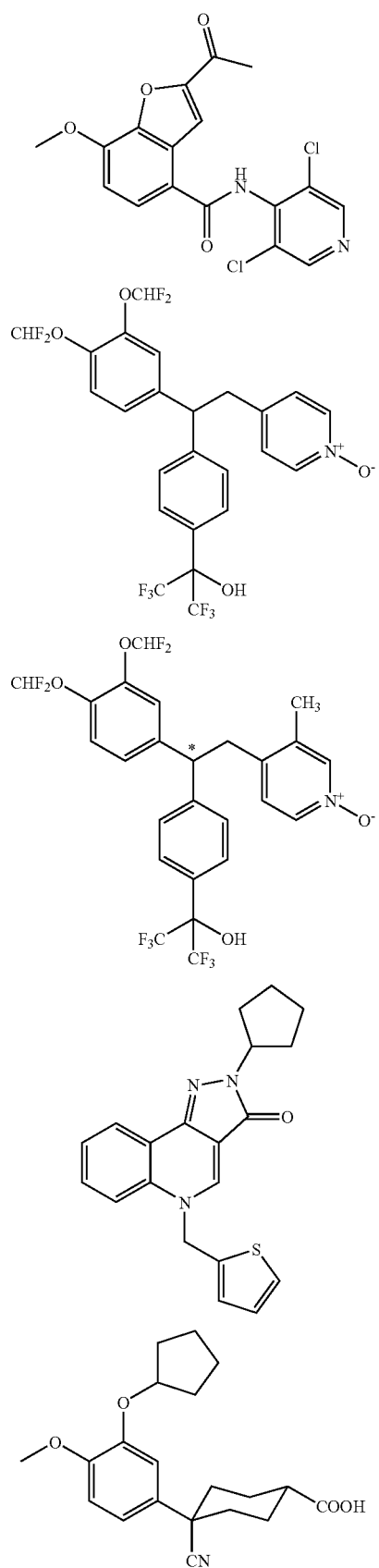

53. The method of claim 3, wherein Z is $CR^3R^4R^5$; each $R^1$, $R^2$ and $R^3$ is hydrogen; $R^4$ and $R^5$ together with the carbon atom to which they are attached form a cycloalkyl ring having 3, 4, 5, 6, 7, 8, 9 or 10 ring atoms; and wherein the ring comprising $R^4$ and $R^5$ is substituted with —$(CH_2)_{0-6}$—Y; where Y is —$CH_2OR^a$, —$CO_2R^a$, —$OC(O)R^a$, —$CH_2OC(O)R^a$, —$C(O)NR^bR^c$, —$CH_2SR^a$, —$C(S)OR^a$, —$OC(S)R^a$, —$CH_2OC(S)R^a$ or $C(S)NR^bR^c$ or —$CH_2N(R^a)(R^b)$;

each $R^7$ is independently hydrogen, $(C_1$-$C_8)$alkyl, $(C_3$-$C_8)$ cycloalkyl, aryl or aryl($C_1$-$C_8$)alkylene;

X is —$CH_2OR^a$, —$CO_2R^a$, —$OC(O)R^a$, —$CH_2OC(O)R^a$, —$C(O)NR^bR^c$, —$CH_2SR^a$, —$C(S)OR^a$, —$OC(S)R^a$, —$CH^2OC(S)R^a$ or $C(S)NR^bR^c$ or —$CH_2N(R^b)(R^c)$;

each $R^a$, $R^b$ and $R^c$ is independently hydrogen, $(C_1$-$C_8)$ alkyl, or $(C_1$-$C_8)$alkyl substituted with 1-3 $(C_1$-$C_8)$ alkoxy, $(C_3$-$C_8)$cycloalkyl, $(C_1$-$C_8)$alkylthio, amino acid, aryl, aryl($C_1$-$C_8$)alkylene, heteroaryl, or heteroaryl $(C_1$-$C_8)$alkylene; or $R^b$ and $R^c$, together with the nitrogen to which they are attached, form a pyrrolidino, piperidino, morpholino, or thiomorpholino ring; and m is 0 to about 6;

or a pharmaceutically acceptable salt thereof.

54. The method of claim 3, wherein the $A_{2A}$ adenosine receptor agonist is ATL-146e, AB-1, AB-3 or JR-3213.

55. The method of claim 3, wherein the $A_{2A}$ adenosine receptor agonist is ATL-146e.

56. The method of claim 2, wherein Type IV phosphodiesterase inhibitor is rolipram or a pharmaceutically acceptable salt thereof.

57. The method of any of claim 2, wherein Type IV phosphodiesterase inhibitor is selected from the group consisting of

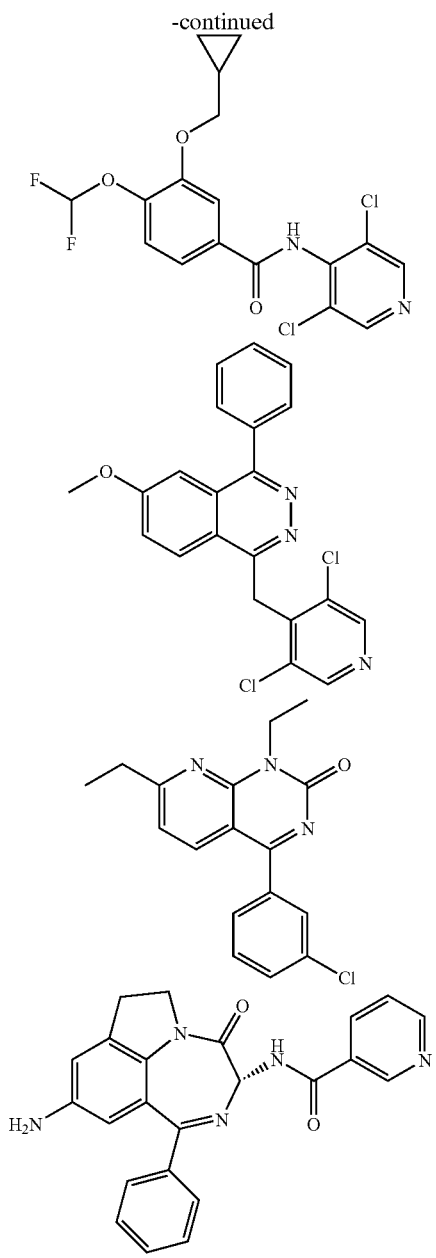
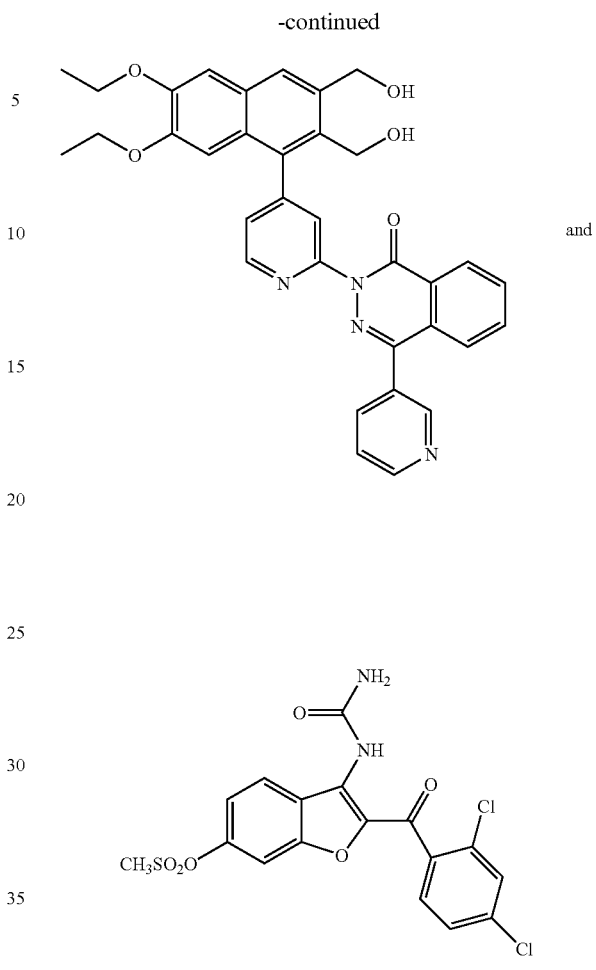
or a pharmaceutically acceptable salt thereof.
58. The method of claims 1 or 2, wherein the effectiveness of the adenosine $A_{2A}$ agonist is blocked by the selective adenosine $A_{2A}$ receptor antagonist ZM 241385.
* * * * *